United States Patent
Huh et al.

(10) Patent No.: US 10,526,586 B2
(45) Date of Patent: Jan. 7, 2020

(54) PYRUVATE DEHYDROGENASE VARIANTS, A MICROORGANISM COMPRISING THE SAME AND A METHOD FOR PRODUCING L-AMINO ACID USING THE SAME

(71) Applicant: CJ CHEILJEDANG CORPORATION, Seoul (KR)

(72) Inventors: Lan Huh, Anyang-si (KR); Jun Ok Moon, Yongin-Si (KR); Hyun Won Bae, Yongin-si (KR); Hyung Joon Kim, Seoul (KR); Sung Ki Song, Bucheon-si (KR)

(73) Assignee: CJ CHEILJEDANG CORPORATION, Seoul (KR)

(*) Notice: Subject to any disclaimer, the term of this patent is extended or adjusted under 35 U.S.C. 154(b) by 0 days.

(21) Appl. No.: 15/557,013

(22) PCT Filed: Mar. 15, 2016

(86) PCT No.: PCT/KR2016/002594
§ 371 (c)(1),
(2) Date: Sep. 8, 2017

(87) PCT Pub. No.: WO2016/148490
PCT Pub. Date: Sep. 22, 2016

(65) Prior Publication Data
US 2018/0057798 A1    Mar. 1, 2018

(30) Foreign Application Priority Data
Mar. 18, 2015    (KR) .................. 10-2015-0037654

(51) Int. Cl.
| C12N 9/02 | (2006.01) |
| C12N 1/20 | (2006.01) |
| C12N 15/53 | (2006.01) |
| C12P 13/04 | (2006.01) |
| C12N 15/77 | (2006.01) |
| C12P 13/08 | (2006.01) |

(52) U.S. Cl.
CPC .......... *C12N 9/0008* (2013.01); *C12N 15/77* (2013.01); *C12P 13/04* (2013.01); *C12P 13/08* (2013.01); *C12Y 102/04001* (2013.01)

(58) Field of Classification Search
None
See application file for complete search history.

(56) References Cited

U.S. PATENT DOCUMENTS

2009/0280542 A1   11/2009   Bathe et al.

FOREIGN PATENT DOCUMENTS

| CN | 104004678 A | 8/2014 |
| EP | 1 219 712 A1 | 7/2002 |
| EP | 1 767 616 A2 | 8/2006 |
| KR | 10-19940001307 B1 | 2/1994 |
| KR | 10-01598120000 B1 | 8/1998 |
| KR | 10-09240650000 B1 | 10/2009 |
| KR | 10-11170220000 B1 | 2/2012 |
| KR | 10-20140111421 A | 9/2014 |

OTHER PUBLICATIONS

GenBank Database Accession No. WP_040086344, Feb. 2016, 2 pages (Year: 2016).*
GenBank Database Accession No. WP_085208706, Apr. 2017, 1 page (Year: 2017).*
Binder et al., "A high-throughput approach to identify genomic variants of bacterial metabolite producers at the single-cell level," *Genome Biology* 13:R40 (12 pages) (2012).
Blombach et al., "$_L$-Valine Production with Pyruvate Dehydrogenase Complex-Deficient *Corynebacterium glutamicum*," *Applied and Environmental Microbiology* 73(7):2079-2084 (Apr. 2007).
Blombach et al., "Effect of pyruvate dehydrogenase complex deficiency on $_L$-lysine production with *Corynebacterium glutamicum*," *Appl Microbiol Biotechnol* 76:615-623 (2007).
Buchholz et al., "Platform Engineering of *Corynebacterium glutamicum* with Reduced Pyruvate Dehydrogenase Complex Activity for Improved Production of $_L$-Lysine, $_L$-Valine, and 2-Ketoisovalerate," *Applied and Environmental Microbiology* 79(18):5566-5575 (Sep. 2013).
Schreiner et al., "E1 Enzyme of the Pyruvate Dehydrogenase Complex in *Corynebacterium glutamicum*: Molecular Analysis of the Gene and Phylogenetic Aspects," *Journal of Bacteriology* 187(17):6005-6018 (Sep. 2005).
Van der Rest et al., "A heat shock following electroporation induces highly efficient transformation of *Corynebacterium glutamicum* with xenogenic plasmid DNA," *Appl Microl Biotechnol* 52:541-545 (1999).
NCBI Reference Sequence: WP_011014985.1 (1 page) (Jul. 18, 2013).
UniParc—UPI000245B513, http://www.uniprot.org/uniparc/UPI000245B513, Jun. 25, 2018 (3 pages).

* cited by examiner

*Primary Examiner* — David Steadman
(74) *Attorney, Agent, or Firm* — Seed IP Law Group LLP

(57) ABSTRACT

The present disclosure relates to a novel pyruvate dehydrogenase variant, a polynucleotide encoding the pyruvate dehydrogenase variant, a microorganism of the genus *Corynebacterium* producing L-amino acid, which includes the pyruvate dehydrogenase variant, and a method for producing an L-amino acid using the microorganism.

11 Claims, No Drawings
Specification includes a Sequence Listing.

SEQUENCE LISTING

```
<160> NUMBER OF SEQ ID NOS: 33

<210> SEQ ID NO 1
<211> LENGTH: 922
<212> TYPE: PRT
<213> ORGANISM: Corynebacterium glutamicum ATCC13032

<400> SEQUENCE: 1

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
        50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
```

```
                      85                  90                  95
    Glu Glu Met Glu Lys Arg Tyr Arg Arg Trp Ile Arg Trp Asn Ala Ala
                    100                 105                 110

Ile Met Val His Arg Ala Gln Arg Pro Gly Ile Gly Val Gly Gly His
                    115                 120                 125

Ile Ser Thr Tyr Ala Gly Ala Ala Pro Leu Tyr Glu Val Gly Phe Asn
                    130                 135                 140

His Phe Phe Arg Gly Lys Asp His Pro Gly Gly Asp Gln Ile Phe
    145                 150                 155                 160

Phe Gln Gly His Ala Ser Pro Gly Met Tyr Ala Arg Ala Phe Met Glu
                    165                 170                 175

Gly Arg Leu Ser Glu Asp Asp Leu Asp Gly Phe Arg Gln Glu Val Ser
                    180                 185                 190

Arg Glu Gln Gly Gly Ile Pro Ser Tyr Pro His Pro His Gly Met Lys
                    195                 200                 205

Asp Phe Trp Glu Phe Pro Thr Val Ser Met Gly Leu Gly Pro Met Asp
                    210                 215                 220

Ala Ile Tyr Gln Ala Arg Phe Asn Arg Tyr Leu Glu Asn Arg Gly Ile
    225                 230                 235                 240

Lys Asp Thr Ser Asp Gln His Val Trp Ala Phe Leu Gly Asp Gly Glu
                    245                 250                 255

Met Asp Glu Pro Glu Ser Arg Gly Leu Ile Gln Gln Ala Ala Leu Asn
                    260                 265                 270

Asn Leu Asp Asn Leu Thr Phe Val Val Asn Cys Asn Leu Gln Arg Leu
                    275                 280                 285

Asp Gly Pro Val Arg Gly Asn Thr Lys Ile Ile Gln Glu Leu Glu Ser
                    290                 295                 300

Phe Phe Arg Gly Ala Gly Trp Ser Val Ile Lys Val Val Trp Gly Arg
    305                 310                 315                 320

Glu Trp Asp Glu Leu Leu Glu Lys Asp Gln Asp Gly Ala Leu Val Glu
                    325                 330                 335

Ile Met Asn Asn Thr Ser Asp Gly Asp Tyr Gln Thr Phe Lys Ala Asn
                    340                 345                 350

Asp Gly Ala Tyr Val Arg Glu His Phe Phe Gly Arg Asp Pro Arg Thr
                    355                 360                 365

Ala Lys Leu Val Glu Asn Met Thr Asp Glu Glu Ile Trp Lys Leu Pro
                    370                 375                 380

Arg Gly Gly His Asp Tyr Arg Lys Val Tyr Ala Ala Tyr Lys Arg Ala
    385                 390                 395                 400

Leu Glu Thr Lys Asp Arg Pro Thr Val Ile Leu Ala His Thr Ile Lys
                    405                 410                 415

Gly Tyr Gly Leu Gly His Asn Phe Glu Gly Arg Asn Ala Thr His Gln
                    420                 425                 430

Met Lys Lys Leu Thr Leu Asp Asp Leu Lys Leu Phe Arg Asp Lys Gln
                    435                 440                 445

Gly Ile Pro Ile Thr Asp Glu Gln Leu Glu Lys Asp Pro Tyr Leu Pro
                    450                 455                 460

Pro Tyr Tyr His Pro Gly Glu Asp Ala Pro Glu Ile Lys Tyr Met Lys
    465                 470                 475                 480

Glu Arg Arg Ala Ala Leu Gly Gly Tyr Leu Pro Glu Arg Arg Glu Asn
                    485                 490                 495

Tyr Asp Pro Ile Gln Val Pro Pro Leu Asp Lys Leu Arg Ser Val Arg
                    500                 505                 510
```

```
Lys Gly Ser Gly Lys Gln Gln Ile Ala Thr Thr Met Ala Thr Val Arg
            515                 520                 525

Thr Phe Lys Glu Leu Met Arg Asp Lys Gly Leu Ala Asp Arg Leu Val
        530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
        595                 600                 605

Ala Gly Thr Ser Tyr Ala Thr His Gly Lys Ala Met Ile Pro Leu Tyr
610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920
```

<210> SEQ ID NO 2
<211> LENGTH: 2769
<212> TYPE: DNA
<213> ORGANISM: Corynebacterium glutamicum ATCC13032

<400> SEQUENCE: 2

| | | | | | |
|---|---|---|---|---|---|
| atggccgatc | aagcaaaact | tggtggcaag | ccctcggatg | actctaactt | cgcgatgatc | 60 |
| cgcgatggcg | tggcatctta | tttgaacgac | tcagatccgg | aggagaccaa | cgagtggatg | 120 |
| gattcactcg | acggattact | ccaggagtct | tctccagaac | gtgctcgtta | cctcatgctt | 180 |
| cgtttgcttg | agcgtgcatc | tgcaaagcgc | gtatctcttc | ccccaatgac | gtcaaccgac | 240 |
| tacgtcaaca | ccattccaac | ctctatggaa | cctgaattcc | caggcgatga | ggaaatggag | 300 |
| aagcgttacc | gtcgttggat | cgctggaacg | cagccatca | tggttcaccg | cgctcagcga | 360 |
| ccaggcatcg | gcgtcggcgg | acacatttcc | acttacgcag | gcgcagcccc | tctgtacgaa | 420 |
| gttggcttca | accacttctt | ccgcggcaag | gatcacccag | gcggcggcga | ccagatcttc | 480 |
| ttccagggcc | acgcatcacc | aggtatgtac | gcacgtgcat | tcatggaggg | tcgcctttct | 540 |
| gaagacgatc | tcgatggctt | ccgtcaggaa | gtttcccgtg | agcagggtgg | cattccgtcc | 600 |
| taccctcacc | cacacggtat | gaaggacttc | tgggagttcc | caactgtgtc | catgggtctt | 660 |
| ggcccaatgg | atgccattta | ccaggcacgt | ttcaaccgct | acctcgaaaa | ccgtggcatc | 720 |
| aaggacacct | ctgaccagca | cgtctgggcc | ttccttggcg | acggcgaaat | ggacgagcca | 780 |
| gaatcacgtg | gtctcatcca | gcaggctgca | ctgaacaacc | tggacaacct | gaccttcgtg | 840 |
| gttaactgca | acctgcagcg | tctcgacgga | cctgtccgcg | gtaacaccaa | gatcatccag | 900 |
| gaactcgagt | ccttcttccg | tggcgcaggc | tggtctgtga | tcaaggttgt | tgggggtcgc | 960 |
| gagtgggatg | aacttctgga | gaaggaccag | gatggtgcac | ttgttgagat | catgaacaac | 1020 |
| acctccgatg | gtgactacca | gaccttcaag | gctaacgacg | gcgcatatgt | tcgtgagcac | 1080 |
| ttcttcggac | gtgaccccacg | caccgcaaag | ctcgttgaga | acatgaccga | cgaagaaatc | 1140 |
| tggaagcttc | cacgtggcgg | ccacgattac | cgcaaggttt | acgcagccta | caagcgagct | 1200 |
| cttgagacca | aggatcgccc | aaccgtcatc | cttgctcaca | ccattaaggg | ctacggactc | 1260 |
| ggccacaact | tcgaaggccg | taacgcaacc | caccagatga | agaagctgac | gcttgatgat | 1320 |
| ctgaagttgt | tccgcgacaa | gcagggcatc | ccaatcaccg | atgagcagct | ggagaaggat | 1380 |
| ccttaccttc | ctccttacta | ccacccaggt | gaagacgctc | ctgaaatcaa | gtacatgaag | 1440 |
| gaacgtcgcg | cagcgctcgg | tggctacctg | ccagagcgtc | gtgagaacta | cgatccaatt | 1500 |
| caggttccac | cactggataa | gcttcgctct | gtccgtaagg | gctccggcaa | gcagcagatc | 1560 |
| gctaccacca | tggcgactgt | tcgtaccttc | aaggaactga | tgcgcgataa | gggcttggct | 1620 |
| gatcgccttg | tcccaatcat | tcctgatgag | gcacgtacct | tcggtcttga | ctcttggttc | 1680 |
| ccaaccttga | agatctacaa | cccgcacggt | cagaactacg | tgcctgttga | ccacgacctg | 1740 |
| atgctctcct | accgtgaggc | acctgaagga | cagatcctgc | acgaaggcat | caacgaggct | 1800 |
| ggttccgtgg | catcgttcat | cgctgcgggt | acctcctacg | ccacccacgg | caaggccatg | 1860 |
| attccgctgt | acatcttcta | ctcgatgttc | ggattccagc | gcaccggtga | ctccatctgg | 1920 |
| gcagcagccg | atcagatggc | acgtggcttc | ctcttgggcg | ctaccgcagg | tcgcaccacc | 1980 |
| ctgaccggtg | aaggcctcca | gcacatggat | ggacactccc | ctgtcttggc | ttccaccaac | 2040 |
| gagggtgtcg | agacctacga | cccatccttt | gcgtacgaga | tcgcacacct | ggttcaccgt | 2100 |
| ggcatcgacc | gcatgtacgg | cccaggcaag | ggtgaagatg | ttatctacta | catcaccatc | 2160 |

-continued

| | |
|---|---|
| tacaacgagc caaccccaca gccagctgag ccagaaggac tggacgtaga aggcctgcac | 2220 |
| aagggcatct acctctactc ccgcggtgaa ggcaccggcc atgaggcaaa catcttggct | 2280 |
| tccggtgttg gtatgcagtg ggctctcaag gctgcatcca tccttgaggc tgactacgga | 2340 |
| gttcgtgcca acatttactc cgctacttct tgggttaact tggctcgcga tggcgctgct | 2400 |
| cgtaacaagg cacagctgcg caacccaggt gcagatgctg gcgaggcatt cgtaaccacc | 2460 |
| cagctgaagc agacctccgg cccatacgtt gcagtgtctg acttctccac tgatctgcca | 2520 |
| aaccagatcc gtgaatgggt cccaggcgac tacaccgttc tcggtgcaga tggcttcggt | 2580 |
| ttctctgata cccgcccagc tgctcgtcgc ttcttcaaca tcgacgctga gtccattgtt | 2640 |
| gttgcagtgc tgaactccct ggcacgcgaa ggcaagatcg acgtctccgt tgctgctcag | 2700 |
| gctgctgaga agttcaagtt ggatgatcct acgagtgttt ccgtagatcc aaacgctcct | 2760 |
| gaggaataa | 2769 |

```
<210> SEQ ID NO 3
<211> LENGTH: 18
<212> TYPE: DNA
<213> ORGANISM: Artificial Sequence
<220> FEATURE:
<223> OTHER INFORMATION: Primer 1

<400> SEQUENCE: 3
```

| | |
|---|---|
| tgggaccggg aaaccggg | 18 |

```
<210> SEQ ID NO 4
<211> LENGTH: 18
<212> TYPE: DNA
<213> ORGANISM: Artificial Sequence
<220> FEATURE:
<223> OTHER INFORMATION: Primer 2

<400> SEQUENCE: 4
```

| | |
|---|---|
| gatttatctg tcccttga | 18 |

```
<210> SEQ ID NO 5
<211> LENGTH: 36
<212> TYPE: DNA
<213> ORGANISM: Artificial Sequence
<220> FEATURE:
<223> OTHER INFORMATION: Primer 3

<400> SEQUENCE: 5
```

| | |
|---|---|
| gcaggtcgac tctagatgcg attcgcgtca aacgtg | 36 |

```
<210> SEQ ID NO 6
<211> LENGTH: 30
<212> TYPE: DNA
<213> ORGANISM: Artificial Sequence
<220> FEATURE:
<223> OTHER INFORMATION: Primer 4

<400> SEQUENCE: 6
```

| | |
|---|---|
| gtcccttgag gtgatgtgaa tccatccact | 30 |

```
<210> SEQ ID NO 7
<211> LENGTH: 30
<212> TYPE: DNA
<213> ORGANISM: Artificial Sequence
<220> FEATURE:
<223> OTHER INFORMATION: Primer 5
```

<400> SEQUENCE: 7
agtggatgga ttcacatcac ctcaagggac                                    30

<210> SEQ ID NO 8
<211> LENGTH: 36
<212> TYPE: DNA
<213> ORGANISM: Artificial Sequence
<220> FEATURE:
<223> OTHER INFORMATION: Primer 6

<400> SEQUENCE: 8
ccggggatcc tctagacgaa gcgccgtgag caattc                             36

<210> SEQ ID NO 9
<211> LENGTH: 521
<212> TYPE: DNA
<213> ORGANISM: Artificial Sequence
<220> FEATURE:
<223> OTHER INFORMATION: aceE gene fragment comprising 5' end of aceE
      gene

<400> SEQUENCE: 9
gcaggtcgac tctagatgcg attcgcgtca acgtgagag aaacatcaca tctcgcggga    60
aactacccga taattctttg caaaactttg caaagcggaa tgaacatgca gctagtttcc   120
gtagaaatgt tctttaaaaa atccacaaca attgccagga agcacaccga ttgatggata   180
cctgaaatcc cagtgagcgc accgctcccc ttacgtcaca gtctgtaaaa caaatcttcg   240
gtgttgcgta tccttgttaa taacttatgc gttgactcat tcgtgcactt cggcgtgtca   300
caattaggta cgaccaagaa tgggaccggg aaaccgggac gtataaacga aataaaacat   360
tccaacagga ggtgtggaaa tggccgatca agcaaaactt ggtggcaagc cctcggatga   420
ctctaacttc gcgatgatcc gcgatggcgt ggcatcttat ttgaacgact cagatccgga   480
ggagaccaac gagtggatgg attcacatca cctcaaggga c                      521

<210> SEQ ID NO 10
<211> LENGTH: 538
<212> TYPE: DNA
<213> ORGANISM: Artificial Sequence
<220> FEATURE:
<223> OTHER INFORMATION: aceE gene fragment comprising 3' end of aceE
      gene

<400> SEQUENCE: 10
agtggatgga ttcacatcac ctcaagggac agataaatcc cgccgccaga cgttagtctg    60
gcggcgggat tcgtcgtaaa gcaagctctt tttagccgag gaacgccttg tcagacaatg   120
ttgcgccctt gatgttggcg aactcctgca gcaaatcgcg cacagtcaac ttcgacttgg   180
tagcctgatc tgcctggtag acaatctggc cttcatgcat catgatcagg cgattgccca   240
ggcgaattgc ctgttccatg ttgtgcgtga ccataagcgt agtcagattt ccatctgcca   300
cgatcttttc ggtcaaggtg gtcacaagct ctgcacgctg tggatcaagc gctgcggtgt   360
gctcatccaa cagcatgatt ttaggttgag taaaaccagc catcagcagg gacaatgcct   420
gacgctgacc gccagagagc aaaccaactt tggcagtgag cctgttttcc agacccagct   480
caaggcgctc aagttcctgc ttgaattgct cacggcgctt cgtctagagg atccccgg    538

<210> SEQ ID NO 11
<211> LENGTH: 1029
<212> TYPE: DNA
<213> ORGANISM: Artificial Sequence
<220> FEATURE:
<223> OTHER INFORMATION: Delta aceE

<400> SEQUENCE: 11

```
gcaggtcgac tctagatgcg attcgcgtca acgtgagag aaacatcaca tctcgcggga      60
aactacccga taattctttg caaaactttg caaagcggaa tgaacatgca gctagtttcc    120
gtagaaatgt tctttaaaaa atccacaaca attgccagga agcacaccga ttgatggata    180
cctgaaatcc cagtgagcgc accgctcccc ttacgtcaca gtctgtaaaa caaatcttcg    240
gtgttgcgta tccttgttaa taacttatgc gttgactcat tcgtgcactt cggcgtgtca    300
caattaggta cgaccaagaa tgggaccggg aaaccgggac gtataaacga aataaaacat    360
tccaacagga ggtgtggaaa tggccgatca agcaaaactt ggtggcaagc cctcggatga    420
ctctaacttc gcgatgatcc gcgatggcgt ggcatcttat ttgaacgact cagatccgga    480
ggagaccaac gagtggatgg attcacatca cctcaaggga cagataaatc ccgccgccag    540
acgttagtct ggcggcggga ttcgtcgtaa agcaagctct ttttagccga ggaacgcctt    600
gtcagacaat gttgcgccct tgatgttggc gaactcctgc agcaaatcgc gcacagtcaa    660
cttcgacttg gtagcctgat ctgcctggta gacaatctgg ccttcatgca tcatgatcag    720
gcgattgccc aggcgaattg cctgttccat gttgtgcgtg accataagcg tagtcagatt    780
tccatctgcc acgatctttt cggtcaaggt ggtcacaagc tctgcacgct gtggatcaag    840
cgctgcggtg tgctcatcca acagcatgat tttaggttga gtaaaaccag ccatcagcag    900
ggacaatgcc tgacgctgac cgccagagag caaaccaact ttggcagtga gcctgttttc    960
cagacccagc tcaaggcgct caagttcctg cttgaattgc tcacggcgct tcgtctagag   1020
gatccccgg                                                           1029
```

<210> SEQ ID NO 12
<211> LENGTH: 26
<212> TYPE: DNA
<213> ORGANISM: Artificial Sequence
<220> FEATURE:
<223> OTHER INFORMATION: Primer 9

<400> SEQUENCE: 12

```
aatctagatg ggaccgggaa accggg                                          26
```

<210> SEQ ID NO 13
<211> LENGTH: 26
<212> TYPE: DNA
<213> ORGANISM: Artificial Sequence
<220> FEATURE:
<223> OTHER INFORMATION: Primer 10

<400> SEQUENCE: 13

```
aatctagaga tttatctgtc ccttga                                          26
```

<210> SEQ ID NO 14
<211> LENGTH: 922
<212> TYPE: PRT
<213> ORGANISM: Artificial Sequence
<220> FEATURE:
<223> OTHER INFORMATION: E1p(Q432E)

<400> SEQUENCE: 14

```
Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
```

```
                    20                  25                  30
        Pro Glu Glu Thr Asn Glu Trp Met Asp Ser Leu Asp Gly Leu Leu Gln
                        35                  40                  45
        Glu Ser Ser Pro Glu Arg Ala Arg Tyr Leu Met Leu Arg Leu Leu Glu
                    50                  55                  60
        Arg Ala Ser Ala Lys Arg Val Ser Leu Pro Pro Met Thr Ser Thr Asp
        65                  70                  75                  80
        Tyr Val Asn Thr Ile Pro Thr Ser Met Glu Pro Glu Phe Pro Gly Asp
                        85                  90                  95
        Glu Glu Met Glu Lys Arg Tyr Arg Arg Trp Ile Arg Trp Asn Ala Ala
                    100                 105                 110
        Ile Met Val His Arg Ala Gln Arg Pro Gly Ile Gly Val Gly Gly His
                    115                 120                 125
        Ile Ser Thr Tyr Ala Gly Ala Ala Pro Leu Tyr Glu Val Gly Phe Asn
                    130                 135                 140
        His Phe Phe Arg Gly Lys Asp His Pro Gly Gly Gly Asp Gln Ile Phe
        145                 150                 155                 160
        Phe Gln Gly His Ala Ser Pro Gly Met Tyr Ala Arg Ala Phe Met Glu
                        165                 170                 175
        Gly Arg Leu Ser Glu Asp Asp Leu Asp Gly Phe Arg Gln Glu Val Ser
                    180                 185                 190
        Arg Glu Gln Gly Gly Ile Pro Ser Tyr Pro His Pro His Gly Met Lys
                    195                 200                 205
        Asp Phe Trp Glu Phe Pro Thr Val Ser Met Gly Leu Gly Pro Met Asp
                    210                 215                 220
        Ala Ile Tyr Gln Ala Arg Phe Asn Arg Tyr Leu Glu Asn Arg Gly Ile
        225                 230                 235                 240
        Lys Asp Thr Ser Asp Gln His Val Trp Ala Phe Leu Gly Asp Gly Glu
                        245                 250                 255
        Met Asp Glu Pro Glu Ser Arg Gly Leu Ile Gln Gln Ala Ala Leu Asn
                    260                 265                 270
        Asn Leu Asp Asn Leu Thr Phe Val Val Asn Cys Asn Leu Gln Arg Leu
                    275                 280                 285
        Asp Gly Pro Val Arg Gly Asn Thr Lys Ile Ile Gln Glu Leu Glu Ser
                    290                 295                 300
        Phe Phe Arg Gly Ala Gly Trp Ser Val Ile Lys Val Val Trp Gly Arg
        305                 310                 315                 320
        Glu Trp Asp Glu Leu Leu Glu Lys Asp Gln Asp Gly Ala Leu Val Glu
                        325                 330                 335
        Ile Met Asn Asn Thr Ser Asp Gly Asp Tyr Gln Thr Phe Lys Ala Asn
                    340                 345                 350
        Asp Gly Ala Tyr Val Arg Glu His Phe Phe Gly Arg Asp Pro Arg Thr
                    355                 360                 365
        Ala Lys Leu Val Glu Asn Met Thr Asp Glu Glu Ile Trp Lys Leu Pro
                    370                 375                 380
        Arg Gly Gly His Asp Tyr Arg Lys Val Tyr Ala Ala Tyr Lys Arg Ala
        385                 390                 395                 400
        Leu Glu Thr Lys Asp Arg Pro Thr Val Ile Leu Ala His Thr Ile Lys
                        405                 410                 415
        Gly Tyr Gly Leu Gly His Asn Phe Glu Gly Arg Asn Ala Thr His Glu
                    420                 425                 430
        Met Lys Lys Leu Thr Leu Asp Asp Leu Lys Leu Phe Arg Asp Lys Gln
                    435                 440                 445
```

```
Gly Ile Pro Ile Thr Asp Glu Gln Leu Glu Lys Asp Pro Tyr Leu Pro
    450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
        515                 520                 525

Thr Phe Lys Glu Leu Met Arg Asp Lys Gly Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
        595                 600                 605

Ala Gly Thr Ser Tyr Ala Thr His Gly Lys Ala Met Ile Pro Leu Tyr
    610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
    690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
    850                 855                 860
```

```
Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
            915                 920

<210> SEQ ID NO 15
<211> LENGTH: 922
<212> TYPE: PRT
<213> ORGANISM: Artificial Sequence
<220> FEATURE:
<223> OTHER INFORMATION: E1p(E190V)

<400> SEQUENCE: 15

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
            115                 120                 125

Ile Ser Thr Tyr Ala Gly Ala Ala Pro Leu Tyr Glu Val Gly Phe Asn
130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Val Val Ser
            180                 185                 190

Arg Glu Gln Gly Gly Ile Pro Ser Tyr Pro His Pro His Gly Met Lys
            195                 200                 205

Asp Phe Trp Glu Phe Pro Thr Val Ser Met Gly Leu Gly Pro Met Asp
210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
    290                 295                 300
```

```
Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
        325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
        355                 360                 365

Ala Lys Leu Val Glu Asn Met Thr Asp Glu Glu Ile Trp Lys Leu Pro
370                 375                 380

Arg Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Gln
            420                 425                 430

Met Lys Lys Leu Thr Leu Asp Asp Leu Lys Leu Phe Arg Asp Lys Gln
        435                 440                 445

Gly Ile Pro Ile Thr Asp Glu Gln Leu Glu Lys Asp Pro Tyr Leu Pro
450                 455                 460

Pro Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
        515                 520                 525

Thr Phe Lys Glu Leu Met Arg Asp Lys Gly Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
        595                 600                 605

Ala Gly Thr Ser Tyr Ala Thr His Gly Lys Ala Met Ile Pro Leu Tyr
610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
    690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
```

```
                        725                 730                 735
Glu Gly Leu His Lys Gly Ile Tyr Leu Tyr Ser Arg Gly Glu Gly Thr
                740                 745                 750
Gly His Glu Ala Asn Ile Leu Ala Ser Gly Val Gly Met Gln Trp Ala
            755                 760                 765
Leu Lys Ala Ala Ser Ile Leu Glu Ala Asp Tyr Gly Val Arg Ala Asn
    770                 775                 780
Ile Tyr Ser Ala Thr Ser Trp Val Asn Leu Ala Arg Asp Gly Ala Ala
785                 790                 795                 800
Arg Asn Lys Ala Gln Leu Arg Asn Pro Gly Ala Asp Ala Gly Glu Ala
                805                 810                 815
Phe Val Thr Thr Gln Leu Lys Gln Thr Ser Gly Pro Tyr Val Ala Val
                820                 825                 830
Ser Asp Phe Ser Thr Asp Leu Pro Asn Gln Ile Arg Glu Trp Val Pro
                835                 840                 845
Gly Asp Tyr Thr Val Leu Gly Ala Asp Gly Phe Gly Phe Ser Asp Thr
            850                 855                 860
Arg Pro Ala Ala Arg Arg Phe Phe Asn Ile Asp Ala Glu Ser Ile Val
865                 870                 875                 880
Val Ala Val Leu Asn Ser Leu Ala Arg Glu Gly Lys Ile Asp Val Ser
                885                 890                 895
Val Ala Ala Gln Ala Ala Glu Lys Phe Lys Leu Asp Asp Pro Thr Ser
                900                 905                 910
Val Ser Val Asp Pro Asn Ala Pro Glu Glu
            915                 920

<210> SEQ ID NO 16
<211> LENGTH: 922
<212> TYPE: PRT
<213> ORGANISM: Artificial Sequence
<220> FEATURE:
<223> OTHER INFORMATION: E1p(L438P)

<400> SEQUENCE: 16

Met Ala Asp Gln Ala Lys Leu Gly Gly Lys Pro Ser Asp Asp Ser Asn
1               5                   10                  15
Phe Ala Met Ile Arg Asp Gly Val Ala Ser Tyr Leu Asn Asp Ser Asp
                20                  25                  30
Pro Glu Glu Thr Asn Glu Trp Met Asp Ser Leu Asp Gly Leu Leu Gln
            35                  40                  45
Glu Ser Ser Pro Glu Arg Ala Arg Tyr Leu Met Leu Arg Leu Leu Glu
    50                  55                  60
Arg Ala Ser Ala Lys Arg Val Ser Leu Pro Pro Met Thr Ser Thr Asp
65                  70                  75                  80
Tyr Val Asn Thr Ile Pro Thr Ser Met Glu Pro Glu Phe Pro Gly Asp
                85                  90                  95
Glu Glu Met Glu Lys Arg Tyr Arg Arg Trp Ile Arg Trp Asn Ala Ala
                100                 105                 110
Ile Met Val His Arg Ala Gln Arg Pro Gly Ile Gly Val Gly Gly His
            115                 120                 125
Ile Ser Thr Tyr Ala Gly Ala Pro Leu Tyr Glu Val Gly Phe Asn
            130                 135                 140
His Phe Phe Arg Gly Lys Asp His Pro Gly Gly Gly Asp Gln Ile Phe
145                 150                 155                 160
Phe Gln Gly His Ala Ser Pro Gly Met Tyr Ala Arg Ala Phe Met Glu
```

-continued

```
                165                 170                 175
Gly Arg Leu Ser Glu Asp Asp Leu Asp Gly Phe Arg Gln Glu Val Ser
                180                 185                 190
Arg Glu Gln Gly Gly Ile Pro Ser Tyr Pro His Pro His Gly Met Lys
                195                 200                 205
Asp Phe Trp Glu Phe Pro Thr Val Ser Met Gly Leu Gly Pro Met Asp
210                 215                 220
Ala Ile Tyr Gln Ala Arg Phe Asn Arg Tyr Leu Glu Asn Arg Gly Ile
225                 230                 235                 240
Lys Asp Thr Ser Asp Gln His Val Trp Ala Phe Leu Gly Asp Gly Glu
                245                 250                 255
Met Asp Glu Pro Glu Ser Arg Gly Leu Ile Gln Gln Ala Ala Leu Asn
                260                 265                 270
Asn Leu Asp Asn Leu Thr Phe Val Val Asn Cys Asn Leu Gln Arg Leu
                275                 280                 285
Asp Gly Pro Val Arg Gly Asn Thr Lys Ile Ile Gln Glu Leu Glu Ser
                290                 295                 300
Phe Phe Arg Gly Ala Gly Trp Ser Val Ile Lys Val Val Trp Gly Arg
305                 310                 315                 320
Glu Trp Asp Glu Leu Leu Glu Lys Asp Gln Asp Gly Ala Leu Val Glu
                325                 330                 335
Ile Met Asn Asn Thr Ser Asp Gly Asp Tyr Gln Thr Phe Lys Ala Asn
                340                 345                 350
Asp Gly Ala Tyr Val Arg Glu His Phe Phe Gly Arg Asp Pro Arg Thr
                355                 360                 365
Ala Lys Leu Val Glu Asn Met Thr Asp Glu Glu Ile Trp Lys Leu Pro
370                 375                 380
Arg Gly Gly His Asp Tyr Arg Lys Val Tyr Ala Ala Tyr Lys Arg Ala
385                 390                 395                 400
Leu Glu Thr Lys Asp Arg Pro Thr Val Ile Leu Ala His Thr Ile Lys
                405                 410                 415
Gly Tyr Gly Leu Gly His Asn Phe Glu Gly Arg Asn Ala Thr His Gln
                420                 425                 430
Met Lys Lys Leu Thr Pro Asp Leu Lys Leu Phe Arg Asp Lys Gln
                435                 440                 445
Gly Ile Pro Ile Thr Asp Glu Gln Leu Glu Lys Asp Pro Tyr Leu Pro
                450                 455                 460
Pro Tyr Tyr His Pro Gly Glu Asp Ala Pro Glu Ile Lys Tyr Met Lys
465                 470                 475                 480
Glu Arg Arg Ala Ala Leu Gly Gly Tyr Leu Pro Glu Arg Arg Glu Asn
                485                 490                 495
Tyr Asp Pro Ile Gln Val Pro Pro Leu Asp Lys Leu Arg Ser Val Arg
                500                 505                 510
Lys Gly Ser Gly Lys Gln Gln Ile Ala Thr Thr Met Ala Thr Val Arg
                515                 520                 525
Thr Phe Lys Glu Leu Met Arg Asp Lys Gly Leu Ala Asp Arg Leu Val
                530                 535                 540
Pro Ile Ile Pro Asp Glu Ala Arg Thr Phe Gly Leu Asp Ser Trp Phe
545                 550                 555                 560
Pro Thr Leu Lys Ile Tyr Asn Pro His Gly Gln Asn Tyr Val Pro Val
                565                 570                 575
Asp His Asp Leu Met Leu Ser Tyr Arg Glu Ala Pro Glu Gly Gln Ile
                580                 585                 590
```

Leu His Glu Gly Ile Asn Glu Ala Gly Ser Val Ala Ser Phe Ile Ala
            595                 600                 605

Ala Gly Thr Ser Tyr Ala Thr His Gly Lys Ala Met Ile Pro Leu Tyr
        610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
                660                 665                 670

Ser Pro Val Leu Ala Ser Thr Asn Glu Gly Val Glu Thr Tyr Asp Pro
            675                 680                 685

Ser Phe Ala Tyr Glu Ile Ala His Leu Val His Arg Gly Ile Asp Arg
        690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
                820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
    850                 855                 860

Arg Pro Ala Ala Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Pro Thr Ser
                900                 905                 910

Val Ser Val Asp Pro Asn Ala Pro Glu Glu
        915                 920

<210> SEQ ID NO 17
<211> LENGTH: 922
<212> TYPE: PRT
<213> ORGANISM: Artificial Sequence
<220> FEATURE:
<223> OTHER INFORMATION: E1p(Q195H)

<400> SEQUENCE: 17

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
            20                  25                  30

```
Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
        50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
            115                 120                 125

Ile Ser Thr Tyr Ala Gly Ala Ala Pro Leu Tyr Glu Val Gly Phe Asn
        130                 135                 140

His Phe Phe Arg Gly Lys Asp His Pro Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu His Gly Gly Ile Pro Ser Tyr Pro His Pro His Gly Met Lys
        195                 200                 205

Asp Phe Trp Glu Phe Pro Thr Val Ser Met Gly Leu Gly Pro Met Asp
        210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
        355                 360                 365

Ala Lys Leu Val Glu Asn Met Thr Asp Glu Glu Ile Trp Lys Leu Pro
370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Gln
            420                 425                 430

Met Lys Lys Leu Thr Leu Asp Asp Leu Lys Leu Phe Arg Asp Lys Gln
        435                 440                 445
```

```
Gly Ile Pro Ile Thr Asp Glu Gln Leu Glu Lys Asp Pro Tyr Leu Pro
    450                 455                 460
Pro Tyr Tyr His Pro Gly Glu Asp Ala Pro Glu Ile Lys Tyr Met Lys
465                 470                 475                 480
Glu Arg Arg Ala Ala Leu Gly Gly Tyr Leu Pro Glu Arg Arg Glu Asn
                485                 490                 495
Tyr Asp Pro Ile Gln Val Pro Pro Leu Asp Lys Leu Arg Ser Val Arg
            500                 505                 510
Lys Gly Ser Gly Lys Gln Gln Ile Ala Thr Thr Met Ala Thr Val Arg
        515                 520                 525
Thr Phe Lys Glu Leu Met Arg Asp Lys Gly Leu Ala Asp Arg Leu Val
    530                 535                 540
Pro Ile Ile Pro Asp Glu Ala Arg Thr Phe Gly Leu Asp Ser Trp Phe
545                 550                 555                 560
Pro Thr Leu Lys Ile Tyr Asn Pro His Gly Gln Asn Tyr Val Pro Val
                565                 570                 575
Asp His Asp Leu Met Leu Ser Tyr Arg Glu Ala Pro Glu Gly Gln Ile
            580                 585                 590
Leu His Glu Gly Ile Asn Glu Ala Gly Ser Val Ala Ser Phe Ile Ala
        595                 600                 605
Ala Gly Thr Ser Tyr Ala Thr His Gly Lys Ala Met Ile Pro Leu Tyr
    610                 615                 620
Ile Phe Tyr Ser Met Phe Gly Phe Gln Arg Thr Gly Asp Ser Ile Trp
625                 630                 635                 640
Ala Ala Ala Asp Gln Met Ala Arg Gly Phe Leu Leu Gly Ala Thr Ala
                645                 650                 655
Gly Arg Thr Thr Leu Thr Gly Glu Gly Leu Gln His Met Asp Gly His
            660                 665                 670
Ser Pro Val Leu Ala Ser Thr Asn Glu Gly Val Glu Thr Tyr Asp Pro
        675                 680                 685
Ser Phe Ala Tyr Glu Ile Ala His Leu Val His Arg Gly Ile Asp Arg
    690                 695                 700
Met Tyr Gly Pro Gly Lys Gly Glu Asp Val Ile Tyr Tyr Ile Thr Ile
705                 710                 715                 720
Tyr Asn Glu Pro Thr Pro Gln Pro Ala Glu Pro Gly Leu Asp Val
                725                 730                 735
Glu Gly Leu His Lys Gly Ile Tyr Leu Tyr Ser Arg Gly Glu Gly Thr
            740                 745                 750
Gly His Glu Ala Asn Ile Leu Ala Ser Gly Val Gly Met Gln Trp Ala
        755                 760                 765
Leu Lys Ala Ala Ser Ile Leu Glu Ala Asp Tyr Gly Val Arg Ala Asn
    770                 775                 780
Ile Tyr Ser Ala Thr Ser Trp Val Asn Leu Ala Arg Asp Gly Ala Ala
785                 790                 795                 800
Arg Asn Lys Ala Gln Leu Arg Asn Pro Gly Ala Asp Ala Gly Glu Ala
                805                 810                 815
Phe Val Thr Thr Gln Leu Lys Gln Thr Ser Gly Pro Tyr Val Ala Val
            820                 825                 830
Ser Asp Phe Ser Thr Asp Leu Pro Asn Gln Ile Arg Glu Trp Val Pro
        835                 840                 845
Gly Asp Tyr Thr Val Leu Gly Ala Asp Gly Phe Gly Phe Ser Asp Thr
    850                 855                 860
Arg Pro Ala Ala Arg Arg Phe Phe Asn Ile Asp Ala Glu Ser Ile Val
```

-continued

```
865                 870                 875                 880
Val Ala Val Leu Asn Ser Leu Ala Arg Glu Gly Lys Ile Asp Val Ser
                885                 890                 895
Val Ala Ala Gln Ala Ala Glu Lys Phe Lys Leu Asp Asp Pro Thr Ser
                900                 905                 910
Val Ser Val Asp Pro Asn Ala Pro Glu Glu
                915                 920
```

<210> SEQ ID NO 18
<211> LENGTH: 922
<212> TYPE: PRT
<213> ORGANISM: Artificial Sequence
<220> FEATURE:
<223> OTHER INFORMATION: E1p(P199S)

<400> SEQUENCE: 18

```
Met Ala Asp Gln Ala Lys Leu Gly Gly Lys Pro Ser Asp Ser Asn
1               5                   10                  15
Phe Ala Met Ile Arg Asp Gly Val Ala Ser Tyr Leu Asn Asp Ser Asp
                20                  25                  30
Pro Glu Glu Thr Asn Glu Trp Met Asp Ser Leu Asp Gly Leu Leu Gln
            35                  40                  45
Glu Ser Ser Pro Glu Arg Ala Arg Tyr Leu Met Leu Arg Leu Leu Glu
        50                  55                  60
Arg Ala Ser Ala Lys Arg Val Ser Leu Pro Pro Met Thr Ser Thr Asp
65                  70                  75                  80
Tyr Val Asn Thr Ile Pro Thr Ser Met Glu Pro Glu Phe Pro Gly Asp
                85                  90                  95
Glu Glu Met Glu Lys Arg Tyr Arg Arg Trp Ile Arg Trp Asn Ala Ala
            100                 105                 110
Ile Met Val His Arg Ala Gln Arg Pro Gly Ile Gly Val Gly Gly His
        115                 120                 125
Ile Ser Thr Tyr Ala Gly Ala Ala Pro Leu Tyr Glu Val Gly Phe Asn
    130                 135                 140
His Phe Phe Arg Gly Lys Asp His Pro Gly Gly Gly Asp Gln Ile Phe
145                 150                 155                 160
Phe Gln Gly His Ala Ser Pro Gly Met Tyr Ala Arg Ala Phe Met Glu
                165                 170                 175
Gly Arg Leu Ser Glu Asp Asp Leu Asp Gly Phe Arg Gln Glu Val Ser
            180                 185                 190
Arg Glu Gln Gly Gly Ile Ser Ser Tyr Pro His Pro His Gly Met Lys
        195                 200                 205
Asp Phe Trp Glu Phe Pro Thr Val Ser Met Gly Leu Gly Pro Met Asp
    210                 215                 220
Ala Ile Tyr Gln Ala Arg Phe Asn Arg Tyr Leu Glu Asn Arg Gly Ile
225                 230                 235                 240
Lys Asp Thr Ser Asp Gln His Val Trp Ala Phe Leu Gly Asp Gly Glu
                245                 250                 255
Met Asp Glu Pro Glu Ser Arg Gly Leu Ile Gln Gln Ala Ala Leu Asn
            260                 265                 270
Asn Leu Asp Asn Leu Thr Phe Val Val Asn Cys Asn Leu Gln Arg Leu
        275                 280                 285
Asp Gly Pro Val Arg Gly Asn Thr Lys Ile Ile Gln Glu Leu Glu Ser
    290                 295                 300
Phe Phe Arg Gly Ala Gly Trp Ser Val Ile Lys Val Val Trp Gly Arg
```

```
305                 310                 315                 320
Glu Trp Asp Glu Leu Leu Glu Lys Asp Gln Asp Gly Ala Leu Val Glu
                325                 330                 335

Ile Met Asn Asn Thr Ser Asp Gly Asp Tyr Gln Thr Phe Lys Ala Asn
                340                 345                 350

Asp Gly Ala Tyr Val Arg Glu His Phe Phe Gly Arg Asp Pro Arg Thr
                355                 360                 365

Ala Lys Leu Val Glu Asn Met Thr Asp Glu Glu Ile Trp Lys Leu Pro
370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Gln
                420                 425                 430

Met Lys Lys Leu Thr Leu Asp Asp Leu Lys Leu Phe Arg Asp Lys Gln
                435                 440                 445

Gly Ile Pro Ile Thr Asp Glu Gln Leu Glu Lys Asp Pro Tyr Leu Pro
450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
                500                 505                 510

Lys Gly Ser Gly Lys Gln Gln Ile Ala Thr Thr Met Ala Thr Val Arg
                515                 520                 525

Thr Phe Lys Glu Leu Met Arg Asp Lys Gly Leu Ala Asp Arg Leu Val
                530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
                580                 585                 590

Leu His Glu Gly Ile Asn Glu Ala Gly Ser Val Ala Ser Phe Ile Ala
                595                 600                 605

Ala Gly Thr Ser Tyr Ala Thr His Gly Lys Ala Met Ile Pro Leu Tyr
                610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
                660                 665                 670

Ser Pro Val Leu Ala Ser Thr Asn Glu Gly Val Glu Thr Tyr Asp Pro
                675                 680                 685

Ser Phe Ala Tyr Glu Ile Ala His Leu Val His Arg Gly Ile Asp Arg
                690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735
```

-continued

```
Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
    850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920

<210> SEQ ID NO 19
<211> LENGTH: 922
<212> TYPE: PRT
<213> ORGANISM: Artificial Sequence
<220> FEATURE:
<223> OTHER INFORMATION: E1p(K435A)

<400> SEQUENCE: 19

Met Ala Asp Gln Ala Lys Leu Gly Gly Lys Pro Ser Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
    50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175
```

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
            195                 200                 205

Asp Phe Trp Glu Phe Pro Thr Val Ser Met Gly Leu Gly Pro Met Asp
            210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
            245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
            275                 280                 285

Asp Gly Pro Val Arg Gly Asn Thr Lys Ile Ile Gln Glu Leu Glu Ser
            290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
            325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
            355                 360                 365

Ala Lys Leu Val Glu Asn Met Thr Asp Glu Glu Ile Trp Lys Leu Pro
370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
            405                 410                 415

Gly Tyr Gly Leu Gly His Asn Phe Glu Gly Arg Asn Ala Thr His Gln
            420                 425                 430

Met Lys Ala Leu Thr Leu Asp Asp Leu Lys Leu Phe Arg Asp Lys Gln
            435                 440                 445

Gly Ile Pro Ile Thr Asp Glu Gln Leu Glu Lys Asp Pro Tyr Leu Pro
            450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
            485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
            515                 520                 525

Thr Phe Lys Glu Leu Met Arg Asp Lys Gly Leu Ala Asp Arg Leu Val
            530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
            565                 570                 575

Asp His Asp Leu Met Leu Ser Tyr Arg Glu Ala Pro Glu Gly Gln Ile
            580                 585                 590

-continued

Leu His Glu Gly Ile Asn Glu Ala Gly Ser Val Ala Ser Phe Ile Ala
            595                 600                 605

Ala Gly Thr Ser Tyr Ala Thr His Gly Lys Ala Met Ile Pro Leu Tyr
        610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Gly Ala Thr Ala
                645                 650                 655

Gly Arg Thr Thr Leu Thr Gly Glu Gly Leu Gln His Met Asp Gly His
                660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
        690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
        770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
                820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
        850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920

<210> SEQ ID NO 20
<211> LENGTH: 922
<212> TYPE: PRT
<213> ORGANISM: Artificial Sequence
<220> FEATURE:
<223> OTHER INFORMATION: E1p(Q432A)

<400> SEQUENCE: 20

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
            20                  25                  30

-continued

```
Pro Glu Glu Thr Asn Glu Trp Met Asp Ser Leu Asp Gly Leu Leu Gln
             35                  40                  45

Glu Ser Ser Pro Glu Arg Ala Arg Tyr Leu Met Leu Arg Leu Leu Glu
 50                  55                  60

Arg Ala Ser Ala Lys Arg Val Ser Leu Pro Pro Met Thr Ser Thr Asp
 65                  70                  75                  80

Tyr Val Asn Thr Ile Pro Thr Ser Met Glu Pro Glu Phe Pro Gly Asp
                 85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
            115                 120                 125

Ile Ser Thr Tyr Ala Gly Ala Ala Pro Leu Tyr Glu Val Gly Phe Asn
130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
195                 200                 205

Asp Phe Trp Glu Phe Pro Thr Val Ser Met Gly Leu Gly Pro Met Asp
            210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
            275                 280                 285

Asp Gly Pro Val Arg Gly Asn Thr Lys Ile Ile Gln Glu Leu Glu Ser
290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
355                 360                 365

Ala Lys Leu Val Glu Asn Met Thr Asp Glu Glu Ile Trp Lys Leu Pro
370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Ala
            420                 425                 430

Met Lys Lys Leu Thr Leu Asp Asp Leu Lys Leu Phe Arg Asp Lys Gln
435                 440                 445

Gly Ile Pro Ile Thr Asp Glu Gln Leu Glu Lys Asp Pro Tyr Leu Pro
```

```
                  450              455              460
Pro Tyr Tyr His Pro Gly Glu Asp Ala Pro Glu Ile Lys Tyr Met Lys
465              470              475              480

Glu Arg Arg Ala Ala Leu Gly Gly Tyr Leu Pro Glu Arg Arg Glu Asn
                485              490              495

Tyr Asp Pro Ile Gln Val Pro Pro Leu Asp Lys Leu Arg Ser Val Arg
                500              505              510

Lys Gly Ser Gly Lys Gln Gln Ile Ala Thr Thr Met Ala Thr Val Arg
                515              520              525

Thr Phe Lys Glu Leu Met Arg Asp Lys Gly Leu Ala Asp Arg Leu Val
                530              535              540

Pro Ile Ile Pro Asp Glu Ala Arg Thr Phe Gly Leu Asp Ser Trp Phe
545              550              555              560

Pro Thr Leu Lys Ile Tyr Asn Pro His Gly Gln Asn Tyr Val Pro Val
                565              570              575

Asp His Asp Leu Met Leu Ser Tyr Arg Glu Ala Pro Glu Gly Gln Ile
                580              585              590

Leu His Glu Gly Ile Asn Glu Ala Gly Ser Val Ala Ser Phe Ile Ala
                595              600              605

Ala Gly Thr Ser Tyr Ala Thr His Gly Lys Ala Met Ile Pro Leu Tyr
                610              615              620

Ile Phe Tyr Ser Met Phe Gly Phe Gln Arg Thr Gly Asp Ser Ile Trp
625              630              635              640

Ala Ala Ala Asp Gln Met Ala Arg Gly Phe Leu Leu Gly Ala Thr Ala
                645              650              655

Gly Arg Thr Thr Leu Thr Gly Glu Gly Leu Gln His Met Asp Gly His
                660              665              670

Ser Pro Val Leu Ala Ser Thr Asn Glu Gly Val Glu Thr Tyr Asp Pro
                675              680              685

Ser Phe Ala Tyr Glu Ile Ala His Leu Val His Arg Gly Ile Asp Arg
                690              695              700

Met Tyr Gly Pro Gly Lys Gly Glu Asp Val Ile Tyr Tyr Ile Thr Ile
705              710              715              720

Tyr Asn Glu Pro Thr Pro Gln Pro Ala Glu Pro Gly Leu Asp Val
                725              730              735

Glu Gly Leu His Lys Gly Ile Tyr Leu Tyr Ser Arg Gly Glu Gly Thr
                740              745              750

Gly His Glu Ala Asn Ile Leu Ala Ser Gly Val Gly Met Gln Trp Ala
                755              760              765

Leu Lys Ala Ala Ser Ile Leu Glu Ala Asp Tyr Gly Val Arg Ala Asn
770              775              780

Ile Tyr Ser Ala Thr Ser Trp Val Asn Leu Ala Arg Asp Gly Ala Ala
785              790              795              800

Arg Asn Lys Ala Gln Leu Arg Asn Pro Gly Ala Asp Ala Gly Glu Ala
                805              810              815

Phe Val Thr Thr Gln Leu Lys Gln Thr Ser Gly Pro Tyr Val Ala Val
                820              825              830

Ser Asp Phe Ser Thr Asp Leu Pro Asn Gln Ile Arg Glu Trp Val Pro
                835              840              845

Gly Asp Tyr Thr Val Leu Gly Ala Asp Gly Phe Gly Phe Ser Asp Thr
                850              855              860

Arg Pro Ala Ala Arg Arg Phe Phe Asn Ile Asp Ala Glu Ser Ile Val
865              870              875              880
```

```
Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920

<210> SEQ ID NO 21
<211> LENGTH: 922
<212> TYPE: PRT
<213> ORGANISM: Artificial Sequence
<220> FEATURE:
<223> OTHER INFORMATION: E1p(Y418H)

<400> SEQUENCE: 21

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
            20                  25                  30

Pro Glu Glu Thr Asn Glu Trp Met Asp Ser Leu Asp Gly Leu Leu Gln
        35                  40                  45

Glu Ser Ser Pro Glu Arg Ala Arg Tyr Leu Met Leu Arg Leu Leu Glu
    50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
        195                 200                 205

Asp Phe Trp Glu Phe Pro Thr Val Ser Met Gly Leu Gly Pro Met Asp
    210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
    290                 295                 300

Phe Phe Arg Gly Ala Gly Trp Ser Val Ile Lys Val Val Trp Gly Arg
305                 310                 315                 320
```

```
Glu Trp Asp Glu Leu Leu Glu Lys Asp Gln Asp Gly Ala Leu Val Glu
                325                 330                 335
Ile Met Asn Asn Thr Ser Asp Gly Asp Tyr Gln Thr Phe Lys Ala Asn
                340                 345                 350
Asp Gly Ala Tyr Val Arg Glu His Phe Phe Gly Arg Asp Pro Arg Thr
                355                 360                 365
Ala Lys Leu Val Glu Asn Met Thr Asp Glu Glu Ile Trp Lys Leu Pro
                370                 375                 380
Arg Gly Gly His Asp Tyr Arg Lys Val Tyr Ala Ala Tyr Lys Arg Ala
385                 390                 395                 400
Leu Glu Thr Lys Asp Arg Pro Thr Val Ile Leu Ala His Thr Ile Lys
                405                 410                 415
Gly His Gly Leu Gly His Asn Phe Glu Gly Arg Asn Ala Thr His Gln
                420                 425                 430
Met Lys Lys Leu Thr Leu Asp Asp Leu Lys Leu Phe Arg Asp Lys Gln
                435                 440                 445
Gly Ile Pro Ile Thr Asp Glu Gln Leu Glu Lys Asp Pro Tyr Leu Pro
                450                 455                 460
Pro Tyr Tyr His Pro Gly Glu Asp Ala Pro Glu Ile Lys Tyr Met Lys
465                 470                 475                 480
Glu Arg Arg Ala Ala Leu Gly Gly Tyr Leu Pro Glu Arg Arg Glu Asn
                485                 490                 495
Tyr Asp Pro Ile Gln Val Pro Pro Leu Asp Lys Leu Arg Ser Val Arg
                500                 505                 510
Lys Gly Ser Gly Lys Gln Gln Ile Ala Thr Thr Met Ala Thr Val Arg
                515                 520                 525
Thr Phe Lys Glu Leu Met Arg Asp Lys Gly Leu Ala Asp Arg Leu Val
                530                 535                 540
Pro Ile Ile Pro Asp Glu Ala Arg Thr Phe Gly Leu Asp Ser Trp Phe
545                 550                 555                 560
Pro Thr Leu Lys Ile Tyr Asn Pro His Gly Gln Asn Tyr Val Pro Val
                565                 570                 575
Asp His Asp Leu Met Leu Ser Tyr Arg Glu Ala Pro Glu Gly Gln Ile
                580                 585                 590
Leu His Glu Gly Ile Asn Glu Ala Gly Ser Val Ala Ser Phe Ile Ala
                595                 600                 605
Ala Gly Thr Ser Tyr Ala Thr His Gly Lys Ala Met Ile Pro Leu Tyr
                610                 615                 620
Ile Phe Tyr Ser Met Phe Gly Phe Gln Arg Thr Gly Asp Ser Ile Trp
625                 630                 635                 640
Ala Ala Ala Asp Gln Met Ala Arg Gly Phe Leu Leu Gly Ala Thr Ala
                645                 650                 655
Gly Arg Thr Thr Leu Thr Gly Glu Gly Leu Gln His Met Asp Gly His
                660                 665                 670
Ser Pro Val Leu Ala Ser Thr Asn Glu Gly Val Glu Thr Tyr Asp Pro
                675                 680                 685
Ser Phe Ala Tyr Glu Ile Ala His Leu Val His Arg Gly Ile Asp Arg
                690                 695                 700
Met Tyr Gly Pro Gly Lys Gly Glu Asp Val Ile Tyr Tyr Ile Thr Ile
705                 710                 715                 720
Tyr Asn Glu Pro Thr Pro Gln Pro Ala Glu Pro Glu Gly Leu Asp Val
                725                 730                 735
```

```
Glu Gly Leu His Lys Gly Ile Tyr Leu Tyr Ser Arg Gly Glu Gly Thr
                 740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
                820                 825                 830

Ser Asp Phe Ser Thr Asp Leu Pro Asn Gln Ile Arg Glu Trp Val Pro
            835                 840                 845

Gly Asp Tyr Thr Val Leu Gly Ala Asp Gly Phe Gly Phe Ser Asp Thr
        850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
                900                 905                 910

Val Ser Val Asp Pro Asn Ala Pro Glu Glu
                915                 920

<210> SEQ ID NO 22
<211> LENGTH: 922
<212> TYPE: PRT
<213> ORGANISM: Artificial Sequence
<220> FEATURE:
<223> OTHER INFORMATION: E1p(Y201A)

<400> SEQUENCE: 22

Met Ala Asp Gln Ala Lys Leu Gly Gly Lys Pro Ser Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
    50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
                100                 105                 110

Ile Met Val His Arg Ala Gln Arg Pro Gly Ile Gly Val Gly Gly His
            115                 120                 125

Ile Ser Thr Tyr Ala Gly Ala Ala Pro Leu Tyr Glu Val Gly Phe Asn
        130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175
```

```
Gly Arg Leu Ser Glu Asp Asp Leu Asp Gly Phe Arg Gln Glu Val Ser
            180                 185                 190

Arg Glu Gln Gly Gly Ile Pro Ser Ala Pro His Pro His Gly Met Lys
        195                 200                 205

Asp Phe Trp Glu Phe Pro Thr Val Ser Met Gly Leu Gly Pro Met Asp
        210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
        290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
        355                 360                 365

Ala Lys Leu Val Glu Asn Met Thr Asp Glu Glu Ile Trp Lys Leu Pro
    370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Gln
            420                 425                 430

Met Lys Lys Leu Thr Leu Asp Asp Leu Lys Leu Phe Arg Asp Lys Gln
        435                 440                 445

Gly Ile Pro Ile Thr Asp Glu Gln Leu Glu Lys Asp Pro Tyr Leu Pro
    450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
        515                 520                 525

Thr Phe Lys Glu Leu Met Arg Asp Lys Gly Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
```

```
                595                 600                 605
Ala Gly Thr Ser Tyr Ala Thr His Gly Lys Ala Met Ile Pro Leu Tyr
    610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
    690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
    850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920

<210> SEQ ID NO 23
<211> LENGTH: 922
<212> TYPE: PRT
<213> ORGANISM: Artificial Sequence
<220> FEATURE:
<223> OTHER INFORMATION: E1p(N428A)

<400> SEQUENCE: 23

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
```

```
             35                  40                  45
Glu Ser Ser Pro Glu Arg Ala Arg Tyr Leu Met Leu Arg Leu Leu Glu
 50                  55                  60

Arg Ala Ser Ala Lys Arg Val Ser Leu Pro Pro Met Thr Ser Thr Asp
 65                  70                  75                  80

Tyr Val Asn Thr Ile Pro Thr Ser Met Glu Pro Glu Phe Pro Gly Asp
                 85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
            115                 120                 125

Ile Ser Thr Tyr Ala Gly Ala Ala Pro Leu Tyr Glu Val Gly Phe Asn
            130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
            195                 200                 205

Asp Phe Trp Glu Phe Pro Thr Val Ser Met Gly Leu Gly Pro Met Asp
210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
            275                 280                 285

Asp Gly Pro Val Arg Gly Asn Thr Lys Ile Ile Gln Glu Leu Glu Ser
290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
            355                 360                 365

Ala Lys Leu Val Glu Asn Met Thr Asp Glu Glu Ile Trp Lys Leu Pro
            370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Ala Ala Thr His Gln
            420                 425                 430

Met Lys Lys Leu Thr Leu Asp Asp Leu Lys Leu Phe Arg Asp Lys Gln
            435                 440                 445

Gly Ile Pro Ile Thr Asp Glu Gln Leu Glu Lys Asp Pro Tyr Leu Pro
450                 455                 460
```

```
Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
        515                 520                 525

Thr Phe Lys Glu Leu Met Arg Asp Lys Gly Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
        595                 600                 605

Ala Gly Thr Ser Tyr Ala Thr His Gly Lys Ala Met Ile Pro Leu Tyr
    610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
    690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
    850                 855                 860

Arg Pro Ala Ala Arg Arg Phe Phe Asn Ile Asp Ala Glu Ser Ile Val
865                 870                 875                 880
```

```
Val Ala Val Leu Asn Ser Leu Ala Arg Glu Gly Lys Ile Asp Val Ser
                885                 890                 895
Val Ala Ala Gln Ala Ala Glu Lys Phe Lys Leu Asp Asp Pro Thr Ser
            900                 905                 910
Val Ser Val Asp Pro Asn Ala Pro Glu Glu
        915                 920

<210> SEQ ID NO 24
<211> LENGTH: 922
<212> TYPE: PRT
<213> ORGANISM: Artificial Sequence
<220> FEATURE:
<223> OTHER INFORMATION: E190V, Q195H

<400> SEQUENCE: 24

Met Ala Asp Gln Ala Lys Leu Gly Gly Lys Pro Ser Asp Asp Ser Asn
1               5                   10                  15
Phe Ala Met Ile Arg Asp Gly Val Ala Ser Tyr Leu Asn Asp Ser Asp
                20                  25                  30
Pro Glu Glu Thr Asn Glu Trp Met Asp Ser Leu Asp Gly Leu Leu Gln
            35                  40                  45
Glu Ser Ser Pro Glu Arg Ala Arg Tyr Leu Met Leu Arg Leu Leu Glu
    50                  55                  60
Arg Ala Ser Ala Lys Arg Val Ser Leu Pro Pro Met Thr Ser Thr Asp
65                  70                  75                  80
Tyr Val Asn Thr Ile Pro Thr Ser Met Glu Pro Glu Phe Pro Gly Asp
                85                  90                  95
Glu Glu Met Glu Lys Arg Tyr Arg Arg Trp Ile Arg Trp Asn Ala Ala
            100                 105                 110
Ile Met Val His Arg Ala Gln Arg Pro Gly Ile Gly Val Gly Gly His
        115                 120                 125
Ile Ser Thr Tyr Ala Gly Ala Ala Pro Leu Tyr Glu Val Gly Phe Asn
    130                 135                 140
His Phe Phe Arg Gly Lys Asp His Pro Gly Gly Gly Asp Gln Ile Phe
145                 150                 155                 160
Phe Gln Gly His Ala Ser Pro Gly Met Tyr Ala Arg Ala Phe Met Glu
                165                 170                 175
Gly Arg Leu Ser Glu Asp Asp Leu Asp Gly Phe Arg Gln Val Val Ser
            180                 185                 190
Arg Glu His Gly Gly Ile Pro Ser Tyr Pro His Pro His Gly Met Lys
        195                 200                 205
Asp Phe Trp Glu Phe Pro Thr Val Ser Met Gly Leu Gly Pro Met Asp
    210                 215                 220
Ala Ile Tyr Gln Ala Arg Phe Asn Arg Tyr Leu Glu Asn Arg Gly Ile
225                 230                 235                 240
Lys Asp Thr Ser Asp Gln His Val Trp Ala Phe Leu Gly Asp Gly Glu
                245                 250                 255
Met Asp Glu Pro Glu Ser Arg Gly Leu Ile Gln Gln Ala Ala Leu Asn
            260                 265                 270
Asn Leu Asp Asn Leu Thr Phe Val Val Asn Cys Asn Leu Gln Arg Leu
        275                 280                 285
Asp Gly Pro Val Arg Gly Asn Thr Lys Ile Ile Gln Glu Leu Glu Ser
    290                 295                 300
Phe Phe Arg Gly Ala Gly Trp Ser Val Ile Lys Val Val Trp Gly Arg
305                 310                 315                 320
```

```
Glu Trp Asp Glu Leu Leu Glu Lys Asp Gln Asp Gly Ala Leu Val Glu
                325                 330                 335
Ile Met Asn Asn Thr Ser Asp Gly Asp Tyr Gln Thr Phe Lys Ala Asn
                340                 345                 350
Asp Gly Ala Tyr Val Arg Glu His Phe Phe Gly Arg Asp Pro Arg Thr
                355                 360                 365
Ala Lys Leu Val Glu Asn Met Thr Asp Glu Glu Ile Trp Lys Leu Pro
            370                 375                 380
Arg Gly Gly His Asp Tyr Arg Lys Val Tyr Ala Ala Tyr Lys Arg Ala
385                 390                 395                 400
Leu Glu Thr Lys Asp Arg Pro Thr Val Ile Leu Ala His Thr Ile Lys
                405                 410                 415
Gly Tyr Gly Leu Gly His Asn Phe Glu Gly Arg Asn Ala Thr His Gln
                420                 425                 430
Met Lys Lys Leu Thr Leu Asp Asp Leu Lys Leu Phe Arg Asp Lys Gln
            435                 440                 445
Gly Ile Pro Ile Thr Asp Glu Gln Leu Glu Lys Asp Pro Tyr Leu Pro
            450                 455                 460
Pro Tyr His Pro Gly Glu Asp Ala Pro Glu Ile Lys Tyr Met Lys
465                 470                 475                 480
Glu Arg Arg Ala Ala Leu Gly Gly Tyr Leu Pro Arg Arg Glu Asn
                485                 490                 495
Tyr Asp Pro Ile Gln Val Pro Pro Leu Asp Lys Leu Arg Ser Val Arg
                500                 505                 510
Lys Gly Ser Gly Lys Gln Gln Ile Ala Thr Thr Met Ala Thr Val Arg
            515                 520                 525
Thr Phe Lys Glu Leu Met Arg Asp Lys Gly Leu Ala Asp Arg Leu Val
            530                 535                 540
Pro Ile Ile Pro Asp Glu Ala Arg Thr Phe Gly Leu Asp Ser Trp Phe
545                 550                 555                 560
Pro Thr Leu Lys Ile Tyr Asn Pro His Gly Gln Asn Tyr Val Pro Val
                565                 570                 575
Asp His Asp Leu Met Leu Ser Tyr Arg Glu Ala Pro Glu Gly Gln Ile
                580                 585                 590
Leu His Glu Gly Ile Asn Glu Ala Gly Ser Val Ala Ser Phe Ile Ala
            595                 600                 605
Ala Gly Thr Ser Tyr Ala Thr His Gly Lys Ala Met Ile Pro Leu Tyr
            610                 615                 620
Ile Phe Tyr Ser Met Phe Gly Phe Gln Arg Thr Gly Asp Ser Ile Trp
625                 630                 635                 640
Ala Ala Ala Asp Gln Met Ala Arg Gly Phe Leu Leu Gly Ala Thr Ala
                645                 650                 655
Gly Arg Thr Thr Leu Thr Gly Glu Gly Leu Gln His Met Asp Gly His
                660                 665                 670
Ser Pro Val Leu Ala Ser Thr Asn Glu Gly Val Glu Thr Tyr Asp Pro
            675                 680                 685
Ser Phe Ala Tyr Glu Ile Ala His Leu Val His Arg Gly Ile Asp Arg
            690                 695                 700
Met Tyr Gly Pro Gly Lys Gly Glu Asp Val Ile Tyr Tyr Ile Thr Ile
705                 710                 715                 720
Tyr Asn Glu Pro Thr Pro Gln Pro Ala Glu Pro Glu Gly Leu Asp Val
                725                 730                 735
Glu Gly Leu His Lys Gly Ile Tyr Leu Tyr Ser Arg Gly Glu Gly Thr
```

```
                         740                 745                 750
Gly His Glu Ala Asn Ile Leu Ala Ser Gly Val Gly Met Gln Trp Ala
            755                 760                 765

Leu Lys Ala Ala Ser Ile Leu Glu Ala Asp Tyr Gly Val Arg Ala Asn
        770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Pro Thr Ser
            900                 905                 910

Val Ser Val Asp Pro Asn Ala Pro Glu Glu
        915                 920

<210> SEQ ID NO 25
<211> LENGTH: 922
<212> TYPE: PRT
<213> ORGANISM: Artificial Sequence
<220> FEATURE:
<223> OTHER INFORMATION: E190V, P199S

<400> SEQUENCE: 25

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
            20                  25                  30

Pro Glu Glu Thr Asn Glu Trp Met Asp Ser Leu Asp Gly Leu Leu Gln
        35                  40                  45

Glu Ser Ser Pro Glu Arg Ala Arg Tyr Leu Met Leu Arg Leu Leu Glu
    50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Val Val Ser
```

```
                180                 185                 190
Arg Glu Gln Gly Gly Ile Ser Ser Tyr Pro His Pro His Gly Met Lys
            195                 200                 205

Asp Phe Trp Glu Phe Pro Thr Val Ser Met Gly Leu Gly Pro Met Asp
        210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
            245                 250                 255

Met Asp Glu Pro Glu Ser Arg Gly Leu Ile Gln Gln Ala Ala Leu Asn
        260                 265                 270

Asn Leu Asp Asn Leu Thr Phe Val Val Asn Cys Asn Leu Gln Arg Leu
    275                 280                 285

Asp Gly Pro Val Arg Gly Asn Thr Lys Ile Ile Gln Glu Leu Glu Ser
        290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
            325                 330                 335

Ile Met Asn Asn Thr Ser Asp Gly Asp Tyr Gln Thr Phe Lys Ala Asn
        340                 345                 350

Asp Gly Ala Tyr Val Arg Glu His Phe Phe Gly Arg Asp Pro Arg Thr
        355                 360                 365

Ala Lys Leu Val Glu Asn Met Thr Asp Glu Glu Ile Trp Lys Leu Pro
370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
            405                 410                 415

Gly Tyr Gly Leu Gly His Asn Phe Glu Gly Arg Asn Ala Thr His Gln
        420                 425                 430

Met Lys Lys Leu Thr Leu Asp Asp Leu Lys Leu Phe Arg Asp Lys Gln
        435                 440                 445

Gly Ile Pro Ile Thr Asp Glu Gln Leu Glu Lys Asp Pro Tyr Leu Pro
        450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
            485                 490                 495

Tyr Asp Pro Ile Gln Val Pro Pro Leu Asp Lys Leu Arg Ser Val Arg
        500                 505                 510

Lys Gly Ser Gly Lys Gln Ile Ala Thr Thr Met Ala Thr Val Arg
        515                 520                 525

Thr Phe Lys Glu Leu Met Arg Asp Lys Gly Leu Ala Asp Arg Leu Val
        530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
            565                 570                 575

Asp His Asp Leu Met Leu Ser Tyr Arg Glu Ala Pro Glu Gly Gln Ile
        580                 585                 590

Leu His Glu Gly Ile Asn Glu Ala Gly Ser Val Ala Ser Phe Ile Ala
        595                 600                 605
```

```
Ala Gly Thr Ser Tyr Ala Thr His Gly Lys Ala Met Ile Pro Leu Tyr
    610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
    690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
    755                 760                 765

Leu Lys Ala Ala Ser Ile Leu Glu Ala Asp Tyr Gly Val Arg Ala Asn
770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
    835                 840                 845

Gly Asp Tyr Thr Val Leu Gly Ala Asp Gly Phe Gly Phe Ser Asp Thr
850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920
```

<210> SEQ ID NO 26
<211> LENGTH: 922
<212> TYPE: PRT
<213> ORGANISM: Artificial Sequence
<220> FEATURE:
<223> OTHER INFORMATION: Q195H, P199S

<400> SEQUENCE: 26

```
Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
            20                  25                  30

Pro Glu Glu Thr Asn Glu Trp Met Asp Ser Leu Asp Gly Leu Leu Gln
        35                  40                  45
```

-continued

```
Glu Ser Ser Pro Glu Arg Ala Arg Tyr Leu Met Leu Arg Leu Leu Glu
    50                  55                  60
Arg Ala Ser Ala Lys Arg Val Ser Leu Pro Pro Met Thr Ser Thr Asp
65                  70                  75                  80
Tyr Val Asn Thr Ile Pro Thr Ser Met Glu Pro Glu Phe Pro Gly Asp
                85                  90                  95
Glu Glu Met Glu Lys Arg Tyr Arg Arg Trp Ile Arg Trp Asn Ala Ala
            100                 105                 110
Ile Met Val His Arg Ala Gln Arg Pro Gly Ile Gly Val Gly Gly His
        115                 120                 125
Ile Ser Thr Tyr Ala Gly Ala Ala Pro Leu Tyr Glu Val Gly Phe Asn
    130                 135                 140
His Phe Phe Arg Gly Lys Asp His Pro Gly Gly Asp Gln Ile Phe
145                 150                 155                 160
Phe Gln Gly His Ala Ser Pro Gly Met Tyr Ala Arg Ala Phe Met Glu
                165                 170                 175
Gly Arg Leu Ser Glu Asp Asp Leu Asp Gly Phe Arg Gln Glu Val Ser
            180                 185                 190
Arg Glu His Gly Gly Ile Ser Ser Tyr Pro His Pro Gly Met Lys
        195                 200                 205
Asp Phe Trp Glu Phe Pro Thr Val Ser Met Gly Leu Gly Pro Met Asp
    210                 215                 220
Ala Ile Tyr Gln Ala Arg Phe Asn Arg Tyr Leu Glu Asn Arg Gly Ile
225                 230                 235                 240
Lys Asp Thr Ser Asp Gln His Val Trp Ala Phe Leu Gly Asp Gly Glu
                245                 250                 255
Met Asp Glu Pro Glu Ser Arg Gly Leu Ile Gln Gln Ala Ala Leu Asn
            260                 265                 270
Asn Leu Asp Asn Leu Thr Phe Val Val Asn Cys Asn Leu Gln Arg Leu
        275                 280                 285
Asp Gly Pro Val Arg Gly Asn Thr Lys Ile Ile Gln Glu Leu Glu Ser
    290                 295                 300
Phe Phe Arg Gly Ala Gly Trp Ser Val Ile Lys Val Trp Gly Arg
305                 310                 315                 320
Glu Trp Asp Glu Leu Leu Glu Lys Asp Gln Asp Gly Ala Leu Val Glu
                325                 330                 335
Ile Met Asn Asn Thr Ser Asp Gly Asp Tyr Gln Thr Phe Lys Ala Asn
            340                 345                 350
Asp Gly Ala Tyr Val Arg Glu His Phe Phe Gly Arg Asp Pro Arg Thr
        355                 360                 365
Ala Lys Leu Val Glu Asn Met Thr Asp Glu Glu Ile Trp Lys Leu Pro
    370                 375                 380
Arg Gly Gly His Asp Tyr Arg Lys Val Tyr Ala Ala Tyr Lys Arg Ala
385                 390                 395                 400
Leu Glu Thr Lys Asp Arg Pro Thr Val Ile Leu Ala His Thr Ile Lys
                405                 410                 415
Gly Tyr Gly Leu Gly His Asn Phe Glu Gly Arg Asn Ala Thr His Gln
            420                 425                 430
Met Lys Lys Leu Thr Leu Asp Asp Leu Lys Leu Phe Arg Asp Lys Gln
        435                 440                 445
Gly Ile Pro Ile Thr Asp Glu Gln Leu Glu Lys Asp Pro Tyr Leu Pro
    450                 455                 460
```

```
Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
            485                 490                 495

Tyr Asp Pro Ile Gln Val Pro Pro Leu Asp Lys Leu Arg Ser Val Arg
                500                 505                 510

Lys Gly Ser Gly Lys Gln Gln Ile Ala Thr Thr Met Ala Thr Val Arg
            515                 520                 525

Thr Phe Lys Glu Leu Met Arg Asp Lys Gly Leu Ala Asp Arg Leu Val
        530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
        595                 600                 605

Ala Gly Thr Ser Tyr Ala Thr His Gly Lys Ala Met Ile Pro Leu Tyr
            610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
            675                 680                 685

Ser Phe Ala Tyr Glu Ile Ala His Leu Val His Arg Gly Ile Asp Arg
        690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
            805                 810                 815

Phe Val Thr Thr Gln Leu Lys Gln Thr Ser Gly Pro Tyr Val Ala Val
        820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
        850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
```

```
                            885                 890                 895
Val Ala Ala Gln Ala Ala Glu Lys Phe Lys Leu Asp Asp Pro Thr Ser
                    900                 905                 910

Val Ser Val Asp Pro Asn Ala Pro Glu Glu
            915                 920

<210> SEQ ID NO 27
<211> LENGTH: 922
<212> TYPE: PRT
<213> ORGANISM: Artificial Sequence
<220> FEATURE:
<223> OTHER INFORMATION: E190V, Y201A

<400> SEQUENCE: 27

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
        50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Val Val Ser
            180                 185                 190

Arg Glu Gln Gly Gly Ile Pro Ser Ala Pro His Pro His Gly Met Lys
        195                 200                 205

Asp Phe Trp Glu Phe Pro Thr Val Ser Met Gly Leu Gly Pro Met Asp
210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
```

```
            325                 330                 335
Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
            355                 360                 365

Ala Lys Leu Val Glu Asn Met Thr Asp Glu Glu Ile Trp Lys Leu Pro
            370                 375                 380

Arg Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                    405                 410                 415

Gly Tyr Gly Leu Gly His Asn Phe Glu Gly Arg Asn Ala Thr His Gln
                    420                 425                 430

Met Lys Lys Leu Thr Leu Asp Asp Leu Lys Leu Phe Arg Asp Lys Gln
                    435                 440                 445

Gly Ile Pro Ile Thr Asp Glu Gln Leu Glu Lys Asp Pro Tyr Leu Pro
            450                 455                 460

Pro Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                    485                 490                 495

Tyr Asp Pro Ile Gln Val Pro Pro Leu Asp Lys Leu Arg Ser Val Arg
                    500                 505                 510

Lys Gly Ser Gly Lys Gln Gln Ile Ala Thr Thr Met Ala Thr Val Arg
            515                 520                 525

Thr Phe Lys Glu Leu Met Arg Asp Lys Gly Leu Ala Asp Arg Leu Val
530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                    565                 570                 575

Asp His Asp Leu Met Leu Ser Tyr Arg Glu Ala Pro Glu Gly Gln Ile
                    580                 585                 590

Leu His Glu Gly Ile Asn Glu Ala Gly Ser Val Ala Ser Phe Ile Ala
            595                 600                 605

Ala Gly Thr Ser Tyr Ala Thr His Gly Lys Ala Met Ile Pro Leu Tyr
            610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                    645                 650                 655

Gly Arg Thr Thr Leu Thr Gly Glu Gly Leu Gln His Met Asp Gly His
                    660                 665                 670

Ser Pro Val Leu Ala Ser Thr Asn Glu Gly Val Glu Thr Tyr Asp Pro
            675                 680                 685

Ser Phe Ala Tyr Glu Ile Ala His Leu Val His Arg Gly Ile Asp Arg
            690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                    725                 730                 735

Glu Gly Leu His Lys Gly Ile Tyr Leu Tyr Ser Arg Gly Glu Gly Thr
                    740                 745                 750
```

```
Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Asp Ala Gly Glu Ala
                805                 810                 815

Phe Val Thr Thr Gln Leu Lys Gln Thr Ser Gly Pro Tyr Val Ala Val
                820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
        850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Pro Thr Ser
        900                 905                 910

Val Ser Val Asp Pro Asn Ala Pro Glu Glu
        915                 920
```

<210> SEQ ID NO 28
<211> LENGTH: 922
<212> TYPE: PRT
<213> ORGANISM: Artificial Sequence
<220> FEATURE:
<223> OTHER INFORMATION: Q195H, Y201A

<400> SEQUENCE: 28

```
Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
    50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
            115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190
```

-continued

```
Arg Glu His Gly Gly Ile Pro Ser Ala Pro His Pro His Gly Met Lys
            195                 200                 205

Asp Phe Trp Glu Phe Pro Thr Val Ser Met Gly Leu Gly Pro Met Asp
    210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
    290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
        355                 360                 365

Ala Lys Leu Val Glu Asn Met Thr Asp Glu Glu Ile Trp Lys Leu Pro
    370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Asn Ala Thr His Gln
            420                 425                 430

Met Lys Lys Leu Thr Leu Asp Asp Leu Lys Leu Phe Arg Asp Lys Gln
        435                 440                 445

Gly Ile Pro Ile Thr Asp Glu Gln Leu Glu Lys Asp Pro Tyr Leu Pro
    450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
        515                 520                 525

Thr Phe Lys Glu Leu Met Arg Asp Lys Gly Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
        595                 600                 605
```

```
Ala Gly Thr Ser Tyr Ala Thr His Gly Lys Ala Met Ile Pro Leu Tyr
            610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
        675                 680                 685

Ser Phe Ala Tyr Glu Ile Ala His Leu Val His Arg Gly Ile Asp Arg
        690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
        755                 760                 765

Leu Lys Ala Ala Ser Ile Leu Glu Ala Asp Tyr Gly Val Arg Ala Asn
    770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
            820                 825                 830

Ser Asp Phe Ser Thr Asp Leu Pro Asn Gln Ile Arg Glu Trp Val Pro
        835                 840                 845

Gly Asp Tyr Thr Val Leu Gly Ala Asp Gly Phe Gly Phe Ser Asp Thr
    850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Pro Thr Ser
            900                 905                 910

Val Ser Val Asp Pro Asn Ala Pro Glu Glu
        915                 920
```

<210> SEQ ID NO 29
<211> LENGTH: 922
<212> TYPE: PRT
<213> ORGANISM: Artificial Sequence
<220> FEATURE:
<223> OTHER INFORMATION: P199S, Y201A

<400> SEQUENCE: 29

```
Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45
```

```
Glu Ser Ser Pro Glu Arg Ala Arg Tyr Leu Met Leu Arg Leu Leu Glu
    50              55                  60

Arg Ala Ser Ala Lys Arg Val Ser Leu Pro Pro Met Thr Ser Thr Asp
 65              70              75                      80

Tyr Val Asn Thr Ile Pro Thr Ser Met Glu Pro Glu Phe Pro Gly Asp
                 85              90                  95

Glu Glu Met Glu Lys Arg Tyr Arg Arg Trp Ile Arg Trp Asn Ala Ala
            100             105                 110

Ile Met Val His Arg Ala Gln Arg Pro Gly Ile Gly Val Gly Gly His
            115             120             125

Ile Ser Thr Tyr Ala Gly Ala Ala Pro Leu Tyr Glu Val Gly Phe Asn
    130             135                 140

His Phe Phe Arg Gly Lys Asp His Pro Gly Gly Gly Asp Gln Ile Phe
145             150             155                         160

Phe Gln Gly His Ala Ser Pro Gly Met Tyr Ala Arg Ala Phe Met Glu
                165             170                 175

Gly Arg Leu Ser Glu Asp Asp Leu Asp Gly Phe Arg Gln Glu Val Ser
            180             185                 190

Arg Glu Gln Gly Gly Ile Ser Ser Ala Pro His Pro His Gly Met Lys
            195             200             205

Asp Phe Trp Glu Phe Pro Thr Val Ser Met Gly Leu Gly Pro Met Asp
    210             215                 220

Ala Ile Tyr Gln Ala Arg Phe Asn Arg Tyr Leu Glu Asn Arg Gly Ile
225             230                 235                     240

Lys Asp Thr Ser Asp Gln His Val Trp Ala Phe Leu Gly Asp Gly Glu
                245             250                 255

Met Asp Glu Pro Glu Ser Arg Gly Leu Ile Gln Gln Ala Ala Leu Asn
            260             265                 270

Asn Leu Asp Asn Leu Thr Phe Val Val Asn Cys Asn Leu Gln Arg Leu
            275             280             285

Asp Gly Pro Val Arg Gly Asn Thr Lys Ile Ile Gln Glu Leu Glu Ser
            290             295             300

Phe Phe Arg Gly Ala Gly Trp Ser Val Ile Lys Val Val Trp Gly Arg
305             310                 315                     320

Glu Trp Asp Glu Leu Leu Glu Lys Asp Gln Asp Gly Ala Leu Val Glu
            325             330                 335

Ile Met Asn Asn Thr Ser Asp Gly Asp Tyr Gln Thr Phe Lys Ala Asn
            340             345                 350

Asp Gly Ala Tyr Val Arg Glu His Phe Phe Gly Arg Asp Pro Arg Thr
            355             360             365

Ala Lys Leu Val Glu Asn Met Thr Asp Glu Glu Ile Trp Lys Leu Pro
    370             375                 380

Arg Gly Gly His Asp Tyr Arg Lys Val Tyr Ala Ala Tyr Lys Arg Ala
385             390             395                     400

Leu Glu Thr Lys Asp Arg Pro Thr Val Ile Leu Ala His Thr Ile Lys
            405                 410                 415

Gly Tyr Gly Leu Gly His Asn Phe Glu Gly Arg Asn Ala Thr His Gln
            420             425                 430

Met Lys Lys Leu Thr Leu Asp Asp Leu Lys Leu Phe Arg Asp Lys Gln
            435             440                 445

Gly Ile Pro Ile Thr Asp Glu Gln Leu Glu Lys Asp Pro Tyr Leu Pro
    450             455                 460

Pro Tyr Tyr His Pro Gly Glu Asp Ala Pro Glu Ile Lys Tyr Met Lys
```

-continued

```
            465                 470                 475                 480
        Glu Arg Arg Ala Ala Leu Gly Gly Tyr Leu Pro Glu Arg Arg Glu Asn
                        485                 490                 495
        Tyr Asp Pro Ile Gln Val Pro Pro Leu Asp Lys Leu Arg Ser Val Arg
                        500                 505                 510
        Lys Gly Ser Gly Lys Gln Gln Ile Ala Thr Thr Met Ala Thr Val Arg
                        515                 520                 525
        Thr Phe Lys Glu Leu Met Arg Asp Lys Gly Leu Ala Asp Arg Leu Val
                        530                 535                 540
        Pro Ile Ile Pro Asp Glu Ala Arg Thr Phe Gly Leu Asp Ser Trp Phe
        545                 550                 555                 560
        Pro Thr Leu Lys Ile Tyr Asn Pro His Gly Gln Asn Tyr Val Pro Val
                        565                 570                 575
        Asp His Asp Leu Met Leu Ser Tyr Arg Glu Ala Pro Glu Gly Gln Ile
                        580                 585                 590
        Leu His Glu Gly Ile Asn Glu Ala Gly Ser Val Ala Ser Phe Ile Ala
                        595                 600                 605
        Ala Gly Thr Ser Tyr Ala Thr His Gly Lys Ala Met Ile Pro Leu Tyr
                        610                 615                 620
        Ile Phe Tyr Ser Met Phe Gly Phe Gln Arg Thr Gly Asp Ser Ile Trp
        625                 630                 635                 640
        Ala Ala Ala Asp Gln Met Ala Arg Gly Phe Leu Leu Gly Ala Thr Ala
                        645                 650                 655
        Gly Arg Thr Thr Leu Thr Gly Glu Gly Leu Gln His Met Asp Gly His
                        660                 665                 670
        Ser Pro Val Leu Ala Ser Thr Asn Glu Gly Val Glu Thr Tyr Asp Pro
                        675                 680                 685
        Ser Phe Ala Tyr Glu Ile Ala His Leu Val His Arg Gly Ile Asp Arg
                        690                 695                 700
        Met Tyr Gly Pro Gly Lys Gly Glu Asp Val Ile Tyr Tyr Ile Thr Ile
        705                 710                 715                 720
        Tyr Asn Glu Pro Thr Pro Gln Pro Ala Glu Pro Glu Gly Leu Asp Val
                        725                 730                 735
        Glu Gly Leu His Lys Gly Ile Tyr Leu Tyr Ser Arg Gly Glu Gly Thr
                        740                 745                 750
        Gly His Glu Ala Asn Ile Leu Ala Ser Gly Val Gly Met Gln Trp Ala
                        755                 760                 765
        Leu Lys Ala Ala Ser Ile Leu Glu Ala Asp Tyr Gly Val Arg Ala Asn
                        770                 775                 780
        Ile Tyr Ser Ala Thr Ser Trp Val Asn Leu Ala Arg Asp Gly Ala Ala
        785                 790                 795                 800
        Arg Asn Lys Ala Gln Leu Arg Asn Pro Gly Ala Asp Ala Gly Glu Ala
                        805                 810                 815
        Phe Val Thr Thr Gln Leu Lys Gln Thr Ser Gly Pro Tyr Val Ala Val
                        820                 825                 830
        Ser Asp Phe Ser Thr Asp Leu Pro Asn Gln Ile Arg Glu Trp Val Pro
                        835                 840                 845
        Gly Asp Tyr Thr Val Leu Gly Ala Asp Gly Phe Gly Phe Ser Asp Thr
                        850                 855                 860
        Arg Pro Ala Ala Arg Phe Phe Asn Ile Asp Ala Glu Ser Ile Val
        865                 870                 875                 880
        Val Ala Val Leu Asn Ser Leu Ala Arg Glu Gly Lys Ile Asp Val Ser
                        885                 890                 895
```

Val Ala Ala Gln Ala Ala Glu Lys Phe Lys Leu Asp Asp Pro Thr Ser
            900                 905                 910

Val Ser Val Asp Pro Asn Ala Pro Glu Glu
            915                 920

<210> SEQ ID NO 30
<211> LENGTH: 922
<212> TYPE: PRT
<213> ORGANISM: Artificial Sequence
<220> FEATURE:
<223> OTHER INFORMATION: N428A, Q432E

<400> SEQUENCE: 30

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
        50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
        115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
        195                 200                 205

Asp Phe Trp Glu Phe Pro Thr Val Ser Met Gly Leu Gly Pro Met Asp
    210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
        275                 280                 285

Asp Gly Pro Val Arg Gly Asn Thr Lys Ile Ile Gln Glu Leu Glu Ser
    290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335

-continued

Ile Met Asn Asn Thr Ser Asp Gly Asp Tyr Gln Thr Phe Lys Ala Asn
                340                 345                 350

Asp Gly Ala Tyr Val Arg Glu His Phe Phe Gly Arg Asp Pro Arg Thr
                355                 360                 365

Ala Lys Leu Val Glu Asn Met Thr Asp Glu Ile Trp Lys Leu Pro
370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly Tyr Gly Leu Gly His Asn Phe Glu Gly Arg Ala Ala Thr His Glu
                420                 425                 430

Met Lys Lys Leu Thr Leu Asp Asp Leu Lys Leu Phe Arg Asp Lys Gln
                435                 440                 445

Gly Ile Pro Ile Thr Asp Glu Gln Leu Glu Lys Asp Pro Tyr Leu Pro
                450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
                500                 505                 510

Lys Gly Ser Gly Lys Gln Gln Ile Ala Thr Thr Met Ala Thr Val Arg
                515                 520                 525

Thr Phe Lys Glu Leu Met Arg Asp Lys Gly Leu Ala Asp Arg Leu Val
                530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
                580                 585                 590

Leu His Glu Gly Ile Asn Glu Ala Gly Ser Val Ala Ser Phe Ile Ala
                595                 600                 605

Ala Gly Thr Ser Tyr Ala Thr His Gly Lys Ala Met Ile Pro Leu Tyr
                610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
                660                 665                 670

Ser Pro Val Leu Ala Ser Thr Asn Glu Gly Val Glu Thr Tyr Asp Pro
                675                 680                 685

Ser Phe Ala Tyr Glu Ile Ala His Leu Val His Arg Gly Ile Asp Arg
                690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Gly Leu Asp Val
                725                 730                 735

Glu Gly Leu His Lys Gly Ile Tyr Leu Tyr Ser Arg Gly Glu Gly Thr
                740                 745                 750

```
Gly His Glu Ala Asn Ile Leu Ala Ser Gly Val Gly Met Gln Trp Ala
            755                 760                 765
Leu Lys Ala Ala Ser Ile Leu Glu Ala Asp Tyr Gly Val Arg Ala Asn
        770                 775                 780
Ile Tyr Ser Ala Thr Ser Trp Val Asn Leu Ala Arg Asp Gly Ala Ala
785                 790                 795                 800
Arg Asn Lys Ala Gln Leu Arg Asn Pro Gly Ala Asp Ala Gly Glu Ala
                805                 810                 815
Phe Val Thr Thr Gln Leu Lys Gln Thr Ser Gly Pro Tyr Val Ala Val
            820                 825                 830
Ser Asp Phe Ser Thr Asp Leu Pro Asn Gln Ile Arg Glu Trp Val Pro
        835                 840                 845
Gly Asp Tyr Thr Val Leu Gly Ala Asp Gly Phe Gly Phe Ser Asp Thr
850                 855                 860
Arg Pro Ala Ala Arg Arg Phe Phe Asn Ile Asp Ala Glu Ser Ile Val
865                 870                 875                 880
Val Ala Val Leu Asn Ser Leu Ala Arg Glu Gly Lys Ile Asp Val Ser
                885                 890                 895
Val Ala Ala Gln Ala Ala Glu Lys Phe Lys Leu Asp Asp Pro Thr Ser
            900                 905                 910
Val Ser Val Asp Pro Asn Ala Pro Glu Glu
        915                 920

<210> SEQ ID NO 31
<211> LENGTH: 922
<212> TYPE: PRT
<213> ORGANISM: Artificial Sequence
<220> FEATURE:
<223> OTHER INFORMATION: N428A, K435A

<400> SEQUENCE: 31

Met Ala Asp Gln Ala Lys Leu Gly Gly Lys Pro Ser Asp Asp Ser Asn
1               5                   10                  15
Phe Ala Met Ile Arg Asp Gly Val Ala Ser Tyr Leu Asn Asp Ser Asp
            20                  25                  30
Pro Glu Glu Thr Asn Glu Trp Met Asp Ser Leu Asp Gly Leu Leu Gln
        35                  40                  45
Glu Ser Ser Pro Glu Arg Ala Arg Tyr Leu Met Leu Arg Leu Leu Glu
    50                  55                  60
Arg Ala Ser Ala Lys Val Ser Leu Pro Pro Met Thr Ser Thr Asp
65                  70                  75                  80
Tyr Val Asn Thr Ile Pro Thr Ser Met Glu Pro Glu Phe Pro Gly Asp
                85                  90                  95
Glu Glu Met Glu Lys Arg Tyr Arg Trp Ile Arg Trp Asn Ala Ala
            100                 105                 110
Ile Met Val His Arg Ala Gln Arg Pro Gly Ile Gly Val Gly His
        115                 120                 125
Ile Ser Thr Tyr Ala Gly Ala Pro Leu Tyr Glu Val Gly Phe Asn
    130                 135                 140
His Phe Phe Arg Gly Lys Asp His Pro Gly Gly Asp Gln Ile Phe
145                 150                 155                 160
Phe Gln Gly His Ala Ser Pro Gly Met Tyr Ala Arg Ala Phe Met Glu
                165                 170                 175
Gly Arg Leu Ser Glu Asp Asp Leu Asp Gly Phe Arg Gln Glu Val Ser
            180                 185                 190
```

```
Arg Glu Gln Gly Gly Ile Pro Ser Tyr Pro His Pro Gly Met Lys
            195                 200                 205

Asp Phe Trp Glu Phe Pro Thr Val Ser Met Gly Leu Gly Pro Met Asp
210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
            245                 250                 255

Met Asp Glu Pro Glu Ser Arg Gly Leu Ile Gln Gln Ala Ala Leu Asn
            260                 265                 270

Asn Leu Asp Asn Leu Thr Phe Val Val Asn Cys Asn Leu Gln Arg Leu
            275                 280                 285

Asp Gly Pro Val Arg Gly Asn Thr Lys Ile Ile Gln Glu Leu Glu Ser
            290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
            325                 330                 335

Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
            355                 360                 365

Ala Lys Leu Val Glu Asn Met Thr Asp Glu Glu Ile Trp Lys Leu Pro
            370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
            405                 410                 415

Gly Tyr Gly Leu Gly His Asn Phe Glu Gly Arg Ala Ala Thr His Gln
            420                 425                 430

Met Lys Ala Leu Thr Leu Asp Asp Leu Lys Leu Phe Arg Asp Lys Gln
            435                 440                 445

Gly Ile Pro Ile Thr Asp Glu Gln Leu Glu Lys Asp Pro Tyr Leu Pro
450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
            485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
            515                 520                 525

Thr Phe Lys Glu Leu Met Arg Asp Lys Gly Leu Ala Asp Arg Leu Val
            530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
            565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
            595                 600                 605

Ala Gly Thr Ser Tyr Ala Thr His Gly Lys Ala Met Ile Pro Leu Tyr
```

```
                    610                 615                 620
Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
                660                 665                 670

Ser Pro Val Leu Ala Ser Thr Asn Glu Gly Val Glu Thr Tyr Asp Pro
            675                 680                 685

Ser Phe Ala Tyr Glu Ile Ala His Leu Val His Arg Gly Ile Asp Arg
690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
                740                 745                 750

Gly His Glu Ala Asn Ile Leu Ala Ser Gly Val Gly Met Gln Trp Ala
            755                 760                 765

Leu Lys Ala Ala Ser Ile Leu Glu Ala Asp Tyr Gly Val Arg Ala Asn
770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
                805                 810                 815

Phe Val Thr Thr Gln Leu Lys Gln Thr Ser Gly Pro Tyr Val Ala Val
                820                 825                 830

Ser Asp Phe Ser Thr Asp Leu Pro Asn Gln Ile Arg Glu Trp Val Pro
            835                 840                 845

Gly Asp Tyr Thr Val Leu Gly Ala Asp Gly Phe Gly Phe Ser Asp Thr
850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
                885                 890                 895

Val Ala Ala Gln Ala Ala Glu Lys Phe Lys Leu Asp Asp Pro Thr Ser
                900                 905                 910

Val Ser Val Asp Pro Asn Ala Pro Glu Glu
            915                 920

<210> SEQ ID NO 32
<211> LENGTH: 922
<212> TYPE: PRT
<213> ORGANISM: Artificial Sequence
<220> FEATURE:
<223> OTHER INFORMATION: Y418H, K435A

<400> SEQUENCE: 32

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
                20                  25                  30

Pro Glu Glu Thr Asn Glu Trp Met Asp Ser Leu Asp Gly Leu Leu Gln
            35                  40                  45

Glu Ser Ser Pro Glu Arg Ala Arg Tyr Leu Met Leu Arg Leu Leu Glu
```

```
            50                  55                  60
Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                    85                  90                  95

Glu Glu Met Glu Lys Arg Tyr Arg Arg Trp Ile Arg Trp Asn Ala Ala
                100                 105                 110

Ile Met Val His Arg Ala Gln Arg Pro Gly Ile Gly Val Gly Gly His
                115                 120                 125

Ile Ser Thr Tyr Ala Gly Ala Ala Pro Leu Tyr Glu Val Gly Phe Asn
                130                 135                 140

His Phe Phe Arg Gly Lys Asp His Pro Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
                180                 185                 190

Arg Glu Gln Gly Gly Ile Pro Ser Tyr Pro His Pro His Gly Met Lys
                195                 200                 205

Asp Phe Trp Glu Phe Pro Thr Val Ser Met Gly Leu Gly Pro Met Asp
210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
                260                 265                 270

Asn Leu Asp Asn Leu Thr Phe Val Val Asn Cys Asn Leu Gln Arg Leu
                275                 280                 285

Asp Gly Pro Val Arg Gly Asn Thr Lys Ile Ile Gln Glu Leu Glu Ser
                290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335

Ile Met Asn Asn Thr Ser Asp Gly Asp Tyr Gln Thr Phe Lys Ala Asn
                340                 345                 350

Asp Gly Ala Tyr Val Arg Glu His Phe Phe Gly Arg Asp Pro Arg Thr
                355                 360                 365

Ala Lys Leu Val Glu Asn Met Thr Asp Glu Glu Ile Trp Lys Leu Pro
370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly His Gly Leu Gly His Asn Phe Glu Gly Arg Asn Ala Thr His Gln
                420                 425                 430

Met Lys Ala Leu Thr Leu Asp Asp Leu Lys Leu Phe Arg Asp Lys Gln
                435                 440                 445

Gly Ile Pro Ile Thr Asp Glu Gln Leu Glu Lys Asp Pro Tyr Leu Pro
                450                 455                 460

Pro Tyr Tyr His Pro Gly Glu Asp Ala Pro Glu Ile Lys Tyr Met Lys
465                 470                 475                 480
```

-continued

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
        515                 520                 525

Thr Phe Lys Glu Leu Met Arg Asp Lys Gly Leu Ala Asp Arg Leu Val
    530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
            565                 570                 575

Asp His Asp Leu Met Leu Ser Tyr Arg Glu Ala Pro Glu Gly Gln Ile
        580                 585                 590

Leu His Glu Gly Ile Asn Glu Ala Gly Ser Val Ala Ser Phe Ile Ala
    595                 600                 605

Ala Gly Thr Ser Tyr Ala Thr His Gly Lys Ala Met Ile Pro Leu Tyr
610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
            645                 650                 655

Gly Arg Thr Thr Leu Thr Gly Glu Gly Leu Gln His Met Asp Gly His
        660                 665                 670

Ser Pro Val Leu Ala Ser Thr Asn Glu Gly Val Glu Thr Tyr Asp Pro
    675                 680                 685

Ser Phe Ala Tyr Glu Ile Ala His Leu Val His Arg Gly Ile Asp Arg
690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Gly Leu Asp Val
            725                 730                 735

Glu Gly Leu His Lys Gly Ile Tyr Leu Tyr Ser Arg Gly Glu Gly Thr
        740                 745                 750

Gly His Glu Ala Asn Ile Leu Ala Ser Gly Val Gly Met Gln Trp Ala
    755                 760                 765

Leu Lys Ala Ala Ser Ile Leu Glu Ala Asp Tyr Gly Val Arg Ala Asn
770                 775                 780

Ile Tyr Ser Ala Thr Ser Trp Val Asn Leu Ala Arg Asp Gly Ala Ala
785                 790                 795                 800

Arg Asn Lys Ala Gln Leu Arg Asn Pro Gly Ala Asp Ala Gly Glu Ala
            805                 810                 815

Phe Val Thr Thr Gln Leu Lys Gln Thr Ser Gly Pro Tyr Val Ala Val
        820                 825                 830

Ser Asp Phe Ser Thr Asp Leu Pro Asn Gln Ile Arg Glu Trp Val Pro
    835                 840                 845

Gly Asp Tyr Thr Val Leu Gly Ala Asp Gly Phe Gly Phe Ser Asp Thr
850                 855                 860

Arg Pro Ala Ala Arg Arg Phe Phe Asn Ile Asp Ala Glu Ser Ile Val
865                 870                 875                 880

Val Ala Val Leu Asn Ser Leu Ala Arg Glu Gly Lys Ile Asp Val Ser
            885                 890                 895

```
Val Ala Ala Gln Ala Ala Glu Lys Phe Lys Leu Asp Asp Pro Thr Ser
            900                 905                 910

Val Ser Val Asp Pro Asn Ala Pro Glu Glu
        915                 920

<210> SEQ ID NO 33
<211> LENGTH: 922
<212> TYPE: PRT
<213> ORGANISM: Artificial Sequence
<220> FEATURE:
<223> OTHER INFORMATION: Y418H, Q432A

<400> SEQUENCE: 33

Met Ala Asp Gln Ala Lys Leu Gly Gly Lys Pro Ser Asp Asp Ser Asn
1               5                   10                  15

Phe Ala Met Ile Arg Asp Gly Val Ala Ser Tyr Leu Asn Asp Ser Asp
            20                  25                  30

Pro Glu Glu Thr Asn Glu Trp Met Asp Ser Leu Asp Gly Leu Leu Gln
        35                  40                  45

Glu Ser Ser Pro Glu Arg Ala Arg Tyr Leu Met Leu Arg Leu Leu Glu
    50                  55                  60

Arg Ala Ser Ala Lys Arg Val Ser Leu Pro Pro Met Thr Ser Thr Asp
65                  70                  75                  80

Tyr Val Asn Thr Ile Pro Thr Ser Met Glu Pro Glu Phe Pro Gly Asp
                85                  90                  95

Glu Glu Met Glu Lys Arg Tyr Arg Arg Trp Ile Arg Trp Asn Ala Ala
            100                 105                 110

Ile Met Val His Arg Ala Gln Arg Pro Gly Ile Gly Val Gly Gly His
            115                 120                 125

Ile Ser Thr Tyr Ala Gly Ala Ala Pro Leu Tyr Glu Val Gly Phe Asn
    130                 135                 140

His Phe Phe Arg Gly Lys Asp His Pro Gly Gly Gly Asp Gln Ile Phe
145                 150                 155                 160

Phe Gln Gly His Ala Ser Pro Gly Met Tyr Ala Arg Ala Phe Met Glu
                165                 170                 175

Gly Arg Leu Ser Glu Asp Asp Leu Asp Gly Phe Arg Gln Glu Val Ser
            180                 185                 190

Arg Glu Gln Gly Gly Ile Pro Ser Tyr Pro His Pro His Gly Met Lys
        195                 200                 205

Asp Phe Trp Glu Phe Pro Thr Val Ser Met Gly Leu Gly Pro Met Asp
    210                 215                 220

Ala Ile Tyr Gln Ala Arg Phe Asn Arg Tyr Leu Glu Asn Arg Gly Ile
225                 230                 235                 240

Lys Asp Thr Ser Asp Gln His Val Trp Ala Phe Leu Gly Asp Gly Glu
                245                 250                 255

Met Asp Glu Pro Glu Ser Arg Gly Leu Ile Gln Gln Ala Ala Leu Asn
            260                 265                 270

Asn Leu Asp Asn Leu Thr Phe Val Asn Cys Asn Leu Gln Arg Leu
        275                 280                 285

Asp Gly Pro Val Arg Gly Asn Thr Lys Ile Ile Gln Glu Leu Glu Ser
    290                 295                 300

Phe Phe Arg Gly Ala Gly Trp Ser Val Ile Lys Val Val Trp Gly Arg
305                 310                 315                 320

Glu Trp Asp Glu Leu Leu Glu Lys Asp Gln Asp Gly Ala Leu Val Glu
                325                 330                 335
```

```
Ile Met Asn Asn Thr Ser Asp Gly Asp Tyr Gln Thr Phe Lys Ala Asn
            340                 345                 350

Asp Gly Ala Tyr Val Arg Glu His Phe Phe Gly Arg Asp Pro Arg Thr
            355                 360                 365

Ala Lys Leu Val Glu Asn Met Thr Asp Glu Glu Ile Trp Lys Leu Pro
    370                 375                 380

Arg Gly Gly His Asp Tyr Arg Lys Val Tyr Ala Ala Tyr Lys Arg Ala
385                 390                 395                 400

Leu Glu Thr Lys Asp Arg Pro Thr Val Ile Leu Ala His Thr Ile Lys
                405                 410                 415

Gly His Gly Leu Gly His Asn Phe Glu Gly Arg Asn Ala Thr His Ala
            420                 425                 430

Met Lys Lys Leu Thr Leu Asp Asp Leu Lys Leu Phe Arg Asp Lys Gln
            435                 440                 445

Gly Ile Pro Ile Thr Asp Glu Gln Leu Glu Lys Asp Pro Tyr Leu Pro
            450                 455                 460

Pro Tyr Tyr His Pro Gly Glu Asp Ala Pro Glu Ile Lys Tyr Met Lys
465                 470                 475                 480

Glu Arg Arg Ala Ala Leu Gly Gly Tyr Leu Pro Glu Arg Arg Glu Asn
                485                 490                 495

Tyr Asp Pro Ile Gln Val Pro Pro Leu Asp Lys Leu Arg Ser Val Arg
            500                 505                 510

Lys Gly Ser Gly Lys Gln Gln Ile Ala Thr Thr Met Ala Thr Val Arg
            515                 520                 525

Thr Phe Lys Glu Leu Met Arg Asp Lys Gly Leu Ala Asp Arg Leu Val
            530                 535                 540

Pro Ile Ile Pro Asp Glu Ala Arg Thr Phe Gly Leu Asp Ser Trp Phe
545                 550                 555                 560

Pro Thr Leu Lys Ile Tyr Asn Pro His Gly Gln Asn Tyr Val Pro Val
                565                 570                 575

Asp His Asp Leu Met Leu Ser Tyr Arg Glu Ala Pro Glu Gly Gln Ile
            580                 585                 590

Leu His Glu Gly Ile Asn Glu Ala Gly Ser Val Ala Ser Phe Ile Ala
            595                 600                 605

Ala Gly Thr Ser Tyr Ala Thr His Gly Lys Ala Met Ile Pro Leu Tyr
            610                 615                 620

Ile Phe Tyr Ser Met Phe Gly Phe Gln Arg Thr Gly Asp Ser Ile Trp
625                 630                 635                 640

Ala Ala Ala Asp Gln Met Ala Arg Gly Phe Leu Leu Gly Ala Thr Ala
                645                 650                 655

Gly Arg Thr Thr Leu Thr Gly Glu Gly Leu Gln His Met Asp Gly His
            660                 665                 670

Ser Pro Val Leu Ala Ser Thr Asn Glu Gly Val Glu Thr Tyr Asp Pro
            675                 680                 685

Ser Phe Ala Tyr Glu Ile Ala His Leu Val His Arg Gly Ile Asp Arg
            690                 695                 700

Met Tyr Gly Pro Gly Lys Gly Glu Asp Val Ile Tyr Tyr Ile Thr Ile
705                 710                 715                 720

Tyr Asn Glu Pro Thr Pro Gln Pro Ala Glu Pro Glu Gly Leu Asp Val
                725                 730                 735

Glu Gly Leu His Lys Gly Ile Tyr Leu Tyr Ser Arg Gly Glu Gly Thr
            740                 745                 750

Gly His Glu Ala Asn Ile Leu Ala Ser Gly Val Gly Met Gln Trp Ala
```

-continued

```
              755                 760                 765
Leu Lys Ala Ala Ser Ile Leu Glu Ala Asp Tyr Gly Val Arg Ala Asn
    770                 775                 780
Ile Tyr Ser Ala Thr Ser Trp Val Asn Leu Ala Arg Asp Gly Ala Ala
785                 790                 795                 800
Arg Asn Lys Ala Gln Leu Arg Asn Pro Gly Ala Asp Ala Gly Glu Ala
                805                 810                 815
Phe Val Thr Thr Gln Leu Lys Gln Thr Ser Gly Pro Tyr Val Ala Val
            820                 825                 830
Ser Asp Phe Ser Thr Asp Leu Pro Asn Gln Ile Arg Glu Trp Val Pro
        835                 840                 845
Gly Asp Tyr Thr Val Leu Gly Ala Asp Gly Phe Gly Phe Ser Asp Thr
    850                 855                 860
Arg Pro Ala Ala Arg Arg Phe Phe Asn Ile Asp Ala Glu Ser Ile Val
865                 870                 875                 880
Val Ala Val Leu Asn Ser Leu Ala Arg Glu Gly Lys Ile Asp Val Ser
                885                 890                 895
Val Ala Ala Gln Ala Ala Glu Lys Phe Lys Leu Asp Asp Pro Thr Ser
            900                 905                 910
Val Ser Val Asp Pro Asn Ala Pro Glu Glu
    915                 920
```

PYRUVATE DEHYDROGENASE VARIANTS, A MICROORGANISM COMPRISING THE SAME AND A METHOD FOR PRODUCING L-AMINO ACID USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_431USPC_SEQUENCE_LISTING.txt. The text file is 154 KB, was created on Sep. 4, 2017, and is being submitted electronically via EFS-Web.

TECHNICAL FIELD

The present disclosure relates to a novel pyruvate dehydrogenase variant, a polynucleotide encoding the pyruvate dehydrogenase variant, a microorganism of the genus Corynebacterium, having an ability to produce L-amino acid which comprises the variant, and a method for producing an L-amino acid using the microorganism.

BACKGROUND ART

Pyruvate dehydrogenase multienzyme complex (PDHC) is an enzyme converting pyruvate generated during glycolysis into acetyl-CoA and is an important enzyme for determining carbon introduction to TCA cycle. PDHC consists of pyruvate dehydrogenase (E1p), dihydrolipoamide acetyltransferase (E2p), and dihydrolipoamide dehydrogenase (E3p). Among them, E1p enzyme is encoded by aceE gene. Although the changes in L-lysine production in strain producing L-lysine due to deleting and weakening of aceE gene (Blombach et al., *Appl. Microbiol. Biotechnol.*, 76: 615, 2007; Buchholz J et al., *Appl Environ Microbiol.*, 79 (18): 5566-75, 2013) have been known, there has been no report regarding the E1p variant, which can improve abilities to produce L-amino acid.

DISCLOSURE

Technical Problem

The present inventors have made extensive efforts to develop a E1p variant that can be used in the production of an L-amino acid at high concentration and a microorganism using the same, and as a result, have developed the E1p variant and discovered that the L-amino acid can be produced in high yield from the microorganism containing the E1p variant, thereby completing the present disclosure.

Technical Solution

An object of the present disclosure is to provide a novel pyruvate dehydrogenase variant.

Another object of the present disclosure is to provide a polynucleotide encoding the pyruvate dehydrogenase variant.

A further object of the present disclosure is to provide a microorganism of the genus Corynebacterium producing L-amino acid, which includes the pyruvate dehydrogenase variant.

A still further object of the present disclosure is to provide a method for producing an L-amino acid, including: (a) culturing the microorganism of the genus Corynebacterium producing L-amino acid, which includes the pyruvate dehydrogenase variant, in a medium to produce an L-amino acid; and (b) recovering the L-amino acid from the cultured microorganism or the medium.

Advantageous Effects of the Present Invention

An enzyme with a weakened activity can be obtained using the pyruvate dehydrogenase variant of the present disclosure. As such, an L-amino acid can be produced with high efficiency using the microorganism, which includes the pyruvate dehydrogenase variant with weakened activity, compared to an L-amino acid-producing microorganism, which includes the wild type pyruvate dehydrogenase protein. Additionally, the microorganism of the present disclosure enables an effective production of an L-amino acid while rarely inhibiting the growth of the microorganism, unlike a pyruvate dehydrogenase-deleted microorganism. For example, lysine, as an essential amino acid for animal feed, is required to be produced in a large-scale from the industrial aspect. Therefore, the production of L-lysine with high efficiency as in the present disclosure can reduce the cost for manufacturing animal feed.

BEST MODE

An aspect of the present disclosure provides a pyruvate dehydrogenase variant which includes at least one amino acid substitutions in a region of amino acids at positions from 190 to 205 or in a region of amino acids at positions from 415 to 440 of SEQ ID NO: 1.

As used herein, the term "pyruvate dehydrogenase" refers to one of the enzymes constituting a pyruvate dehydrogenase multienzyme complex (PDHC), which is involved in the conversion of pyruvate into acetyl-CoA. As used herein, pyruvate dehydrogenase is not particularly limited as long as it has the corresponding activity, and it may be a pyruvate dehydrogenase derived from a microorganism of the genus Corynebacterium, specifically, Corynebacterium glutamicum, but is not limited thereto. For example, the pyruvate dehydrogenase may be an amino acid sequence of SEQ ID NO: 1 or an amino acid sequence having a homology of at least 75%, specifically at least 80%, more specifically 85%, and even more specifically 90%, 91%, 92%, 93%, 94%, 95%, 96%, 97%, 98%, or 99% or higher to the amino acid sequence of SEQ ID NO: 1. The E1p protein having the amino acid sequence of SEQ ID NO: 1 may be encoded by aceE gene having the polynucleotide sequence of SEQ ID NO: 2, but is not limited thereto. Additionally, if an amino acid sequence has a homology to the above sequence and has substantially the same or corresponding biological activity to the protein of SEQ ID NO: 1, it is obvious that the amino acid sequence with a deletion, a modification, a substitution, or an addition should also belong to the scope of the present disclosure. In the present disclosure, any polynucleotide sequence encoding pyruvate dehydrogenase may belong to the scope of the present disclosure. For example, the polynucleotide sequence may be a polynucleotide sequence which has a homology of at least 75%, specifically at least 80%, more specifically 85%, and even more specifically 90%, 91%, 92%, 93%, 94%, 95%, 96%, 97%, 98%, or 99% or higher, to the amino acid sequence of SEQ ID NO: 2. Additionally, based on the codon degeneracy or considering the codons preferred by organisms to express the protein, the polynucleotide sequence encoding the protein may have various variants on the coding region within the scope not changing the amino acid sequence of the protein being expressed from the coding region.

The pyruvate dehydrogenase variant according to the present disclosure may include at least one, at least two, at least three, at least four, at least five, at least six, at least seven, at least eight, at least nine, or at least 10 amino acid substitutions in the region of amino acids at positions from 190 to 205 or from 415 to 440 of SEQ ID NO: 1.

In particular, the pyruvate dehydrogenase variant according to the present disclosure may include at least one, at least two, at least three, or at least four amino acid substitutions in the region of amino acids at positions from 190 to 205 of SEQ ID NO: 1. Specifically, the amino acid substitution in the region of amino acids at positions from 190 to 205 of SEQ ID NO: 1 may be selected from the group of amino acids at positions 190, 195, 199, and 201, but is not limited thereto.

The substitution in the region of amino acids at positions from 190 to 205 of SEQ ID NO: 1 may be a substitution of at least one amino acid in the region of amino acids at positions from 190 to 205 with a different kind of an amino acid, more specifically, a substitution of at least one amino acid at positions 190, 195, 199, and 201 with a different kind of an amino acid, and even more specifically, at least one selected from the group consisting of a substitution of glutamic acid at position 190 with valine (E190V), a substitution of glutamine at position 195 with histidine (Q195H), a substitution of proline at position 199 with serine (P199S), and a substitution of tyrosine at position 201 with alanine (Y201A), but is not particularly limited thereto.

Additionally, the pyruvate dehydrogenase variant according to the present disclosure may include at least one, at least two, at least three, at least four, at least five, or at least six amino acid substitutions in the region of amino acids at positions from 415 to 440 of SEQ ID NO: 1. Specifically, the amino acid substitution in the region of amino acids at positions from 415 to 440 of SEQ ID NO: 1 may be selected from the group consisting of amino acids at positions 418, 428, 432, 435, and 438.

The substitution in the region of amino acids at positions from 415 to 440 of SEQ ID NO: 1 may be a substitution of at least one amino acid in the region of amino acids at positions from 415 to 440 with a different kind of an amino acid, specifically, a substitution of at least one amino acid at positions 418, 428, 432, 435, and 438 with a different kind of an amino acid, and even more specifically, at least one selected from the group consisting of a substitution of tyrosine at position 418 with histidine (Y418H), a substitution of asparagine at position 428 with alanine (N428A), a substitution of glutamine at position 432 with glutamic acid (Q432E), a substitution of glutamine at position 432 with alanine (Q432A), a substitution of lysine at position 435 with alanine (K435A), and a substitution of leucine with proline (L438P), but is not particularly limited thereto.

More specifically, the pyruvate dehydrogenase variant may include an amino acid sequence selected from the group consisting of SEQ ID NOS: 14 to 33.

The pyruvate dehydrogenase variant may include not only the proteins having the amino acid sequences of SEQ ID NOS: 14 to 33 but also the pyruvate dehydrogenase variant having a homology of 75% or higher, specifically 80% or higher, more specifically 85% or higher, and even more specifically 90%, 91%, 92%, 93%, 94%, 95%, 96%, 97%, 98%, and 99% or higher, to the amino acid sequences of SEQ ID NOS: 14 to 33, without limitation, as long as their pyruvate dehydrogenase activity is substantially weakened compared to that of the wild type. It is obvious that the amino acid sequences having substantially the same or corresponding biological activity with the proteins having the amino acid sequences of SEQ ID NOS: 14 to 33 should also belong to the scope of the present disclosure, although the amino acid sequences may have a deletion, a modification, a substitution, or an addition, in part of the sequences.

As used herein, the term "homology" refers to a percentage of identity between two polynucleotide or polypeptide moieties. The homology between sequences from a moiety to another moiety may be determined by the technology known in the art. For example, the homology may be determined by directly arranging the sequence information of two polynucleotide molecules or two polypeptide molecules using an easily accessible computer program. Examples of the computer program may include BLAST (NCBI), CLC Main Workbench (CLC bio), MegAlign™ (DNASTAR Inc.), etc. Additionally, the homology between polynucleotides may be determined by hybridizing polynucleotides under the condition of forming a stable double-strand between the homologous regions, disassembling with a single strand-specific nuclease, followed by size determination of the disassembled fragments.

An aspect of the present disclosure provides a polynucleotide encoding the pyruvate dehydrogenase variant.

The pyruvate dehydrogenase variant is the same as explained above. Specifically, the polynucleotide encoding the pyruvate dehydrogenase variant may belong to the scope of the present disclosure as long as the polynucleotide encodes proteins having the amino acid sequences of SEQ ID NOS: 14 to 33. Furthermore, the polynucleotide may be any polynucleotide having a homology of 75% or higher, specifically 80% or higher, more specifically 85% or higher, and even more specifically 90%, 91%, 92%, 93%, 94%, 95%, 96%, 97%, 98%, and 99% or higher, to the above polynucleotide sequence.

As used herein, the term "polynucleotide" refers to a polymer of nucleotides lengthwise chain-extended by a covalent bond of nucleotide units, in general DNA or RNA strand with a certain length, and in the present disclosure, it refers to a polynucleotide encoding the pyruvate dehydrogenase variant. The polynucleotide may have various nucleotide sequences encoding the same amino acid based on codon degeneracy. Additionally, for the optimization of the expression according to the type of host cells, the polynucleotide may have a codon-optimized sequence.

Still another aspect of the present disclosure provides a microorganism of the genus *Corynebacterium* producing L-amino acid, which includes the pyruvate dehydrogenase variant.

Specifically, the microorganism may include the pyruvate dehydrogenase variant by a mutation, or may be one transformed by a vector including a polynucleotide, which encodes the pyruvate dehydrogenase variant.

As used herein, the term "vector" refers to any carrier for cloning and/or transferring bases to a host cell. A vector may be a replicon to allow for the replication of other DNA fragment(s) which combined with the vector. "Replicon" refers to any genetic unit acting as the unit of DNA replication in vivo, that is, genetic units (e.g., plasmids, phages, cosmids, chromosomes, and viruses) replicable by self-regulation. As used herein, the term "vector" is not particularly limited as long as it can replicate in a host, and any vector known in the art may be used. The vector used in the construction of the recombinant vector may be in a natural state or plasmids, cosmids, viruses, and bacteriophages in a recombinant state. For example, as a phage vector or cosmid vector, pWE15, M13, λEMBL3, λEMBL4, λFIXII, λDASHII, λZAPII, λgt10, λgt11, Charon4A, Charon21A, etc., may be used, and as a plasmid vector, those based on pDZ vector, pBR, pUC, pBluescriptII, pGEM, pTZ, pCL, pET, etc., may be used. The vectors that can be used in the present disclosure are not particularly limited but any known expression vector may be used. Specifically, pDZ (Korean Patent No. 10-0924065 is incorporated in its entirety as a reference in the present disclosure) may be used, but is not limited thereto.

As used herein, the term "transformation" refers to a process of introducing a gene into a host cell, thereby enabling the expression of the gene in the host cell. The transformed gene may include, without limitation, any gene whether it is inserted into the chromosome of a host cell and located therein or located outside the chromosome, as long as it can be expressed in the host cell. The polynucleotide may be introduced into a host cell in the form of an expression cassette, which is a polynucleotide construct including all essential elements required for self-expression. The expression cassette may conventionally include a promoter operably connected to the gene, a transcription termination signal, a ribosome-binding domain, and a translation termination signal. The expression cassette may be in the form of an expression vector capable of self-replication. Additionally, the polynucleotide may be introduced into a host cell as it is or in the form of polynucleotide construct and operably connected to a sequence necessary for its expression in the host cell, but is not limited thereto.

The microorganism may be any prokaryotic or eukaryotic microorganism as long as the microorganism includes the activity of the corresponding pyruvate dehydrogenase variant or the microorganism is transformed to express the corresponding protein. Examples of the microorganism may include microbial strains of the genus *Escherichia*, the genus *Envinia*, the genus *Serratia*, the genus *Providencia*, the genus *Enterobacteria*, the genus *Salmonella*, the genus *Streptomyces*, the genus *Pseudomonas*, the genus *Brevibacterium*, the genus *Corynebacterium*, etc., specifically, a microorganism of the genus *Corynebacterium*, and more specifically, *Corynebacterium glutamicum*, but is not limited thereto.

Additionally, when the pyruvate dehydrogenase variant of the present disclosure is included in the microorganism having an ability to produce L-amino acid, the ability to produce L-amino acid can be significantly improved without considerably inhibiting the growth of cells, compared to the microorganism including the wild-type pyruvate dehydrogenase.

As used herein, the term "L-amino acid" refers to all L-amino acids that can be produced from various carbon sources through pyruvate, and specifically, may refer to an L-amino acid which does not go through with a process of converting pyruvate into acetyl CoA in a biosynthetic pathway. More specifically, the L-amino acid may include L-lysine, L-threonine, L-methionine, L-isoleucine, L-valine, L-leucine, or L-alanine, and even more specifically, L-lysine or L-valine.

The microorganism producing L-amino acid may include both eukaryotic and prokaryotic microorganisms that can produce L-amino acid in vivo, and examples of the microorganisms are the same as described above. The microorganism producing L-amino acid may be any microorganism without limitation as long as the microorganism has the ability to produce L-amino acid, including both wild-type strains and recombinant strains.

For example, a microorganism of the genus *Corynebacterium* producing L-lysine may be modified to be resistant to an L-lysine analog or have enhanced activity of the L-lysine biosynthesis-related protein compared to that of unmodified microorganism. Specifically, expression of at least one kind of gene related to L-lysine biosynthesis is improved by gene amplification; substitution or modification of sequences such as a promoter or a start codon; introduction of a modification for the improvement of expression, etc., but is not limited thereto.

Additionally, examples of the L-lysine biosynthesis-related gene may include the genes located on the L-lysine biosynthesis pathway, and specifically, dihydrodipicolinic acid synthasegene (dapA), asparto kinasegene (lysC), dihydrodipicolinic acid reductase gene (dapB), diaminopimelic acid decarboxylase gene (lysA), diaminopimelic acid dehydrogenase gene (ddh), phosphoenolpyruvate carboxykinase gene (ppc), aspartate semialdehyde dehydrogenase gene (asd), aspartase gene (aspB), and pyruvate carboxylase (Pyc), but is not limited thereto. Additionally, examples of the L-lysine biosynthesis-related gene may include transketolase (tkt), etc., present on the pentose phosphate pathway, but is not limited thereto.

In particular, the microorganism of the genus *Corynebacterium* producing L-lysine may exhibit the ability to produce L-lysine by including the modification, which is related to L-lysine production, disclosed in the art, but is not limited thereto.

The microorganism producing L-threonine may be a microorganism, which has a methionine requirement, a resistance to threonine analogs, a resistance to lysine analogs, a resistance to isoleucine analogs, and/or a resistance to methionine analogs, although not particularly limited thereto. Methionine analogs may be at least one compound selected from the group consisting of D,L-ethionine, norleucine, α-methylmethionine, and L-methionine-D,L-sulfoximine; threonine analogs may be at least one compound selected from the group consisting of α-amino-β-hydroxy valeric acid and D,L-threonine hydroxamate; and lysine analogs may be at least one compound selected from the group consisting of S-(2-aminoethyl)-L-cysteine and δ-methyl-L-lysine.

Additionally, the microorganism producing L-threonine may include a microorganism, in which the activity of PckA involved in the conversion of oxaloacetate (OAA), which is an intermediate for L-threonine biosynthesis, into phosphoenolpyruvate (PEP) is weakened or inactivated; or a microorganism, in which the activity of TyrR, which inhibits lysC gene involved in the conversion of oxaloacetate into aspartate is weakened or inactivated; or a microorganism, in which the activity of GalR, which inhibits the expression of galP gene involved in the introduction of glucose is weakened or inactivated, but is not limited thereto.

The microorganism producing L-isoleucine may be a microorganism having a resistance to L-isoleucine or derivatives thereof, or a microorganism which was genetically manipulated to release the feedback inhibition by L-isoleucine or derivatives thereof. Examples of the derivatives of L-isoleucine may include 4-thiaisoleucine (thiaile) and isoleucine-hydroxamate (ileHx), but is not limited thereto.

The microorganism producing L-valine may be a microorganism having a resistance to L-valine or derivatives thereof, or a microorganism in which the enzyme in the biosynthesis pathway of L-valine was genetically manipulated to release the feedback inhibition by L-valine or derivatives thereof. Examples of the microorganism may include a microorganism including an acetohydroxy acid synthase variant, in which the feedback inhibition to L-valine is released, but is not limited thereto. Additionally, the microorganism may be one in which the expression of L-valine operon was modified to be enhanced, and for example, the microorganism may be one in which the expression of L-valine operon was enhanced due to the deletion of a part or entirety of the polynucleotide sequence encoding the leader peptide within the regulation region of L-valine operon (Korean Patent Application Publication No. 10-2014-0111421, the entirety of the specification of which may be incorporated as a reference but is not limited thereto).

In Still another aspect of the present disclosure provides a method for producing L-amino acid, including: (a) culturing the microorganism of the genus *Corynebacterium* producing L-amino acid, which includes the pyruvate dehydrogenase variant, in a medium to produce an L-amino acid; and (b) recovering the L-amino acid from the cultured microorganism or the medium.

The microorganism of the genus *Corynebacterium* producing L-amino acid, etc., are the same as described above.

As used herein, the term "culture" refers to growing the microorganism under appropriately and artificially controlled environmental conditions. The culture process of the present disclosure may be executed based on appropriate culture media and culture conditions known in the art. Specific conditions, such as culture temperature, culture time, pH value of culture medium, etc., may be determined by the general knowledge by one of ordinary skill in the art or the conventional method known in the art, and appropriately adjusted accordingly. Specifically, these known culture methods are described in references in details [Chmiel; Bioprozesstechnik 1. Einfuhrung indie Bioverfahrenstechnik (Gustav Fischer Verlag, Stuttgart, 1991), and Storhas; Bioreaktoren and periphere Einrichtungen (Vieweg Verlag, Braunschweig/Wiesbaden, 1994)]. Additionally, the culture methods may include batch culture, continuous culture, and fed-batch culture, and specifically, the culture may be performed continuously in a fed batch or repeated fed batch process, but are not limited thereto. The medium used in the culture must appropriately satisfy the requirements for specific strains. Examples of the carbon source to be used in the medium may include sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid, but are not limited thereto. These carbon sources may be used alone or in combination but are not limited thereto. Examples of the nitrogen sources to be used in the medium may include peptone, yeast extract, meat gravy, malt extract, corn steep liquor, soybean flour; and urea or inorganic compounds such as ammonium sulfate, ammonium chloride, ammonium phosphate, ammonium carbonate, and ammonium nitrate. These nitrogen sources may also be used alone or in combination, but are not limited thereto. Examples of the phosphorus sources to be used in the medium may include dihydrogen phosphate, dipotassium hydrogen phosphate, corresponding sodium-containing salts, etc., but are not limited thereto. Additionally, metal salts such as magnesium sulfate or iron sulfate required for growth may be contained in the medium. Lastly, essential materials for growth, such as amino acids and vitamins, may also be contained in addition to the materials described above. Additionally, precursors suitable for culture medium may be used. These sources may be added in an appropriate manner during the culture by a batch culture or a continuous culture to a culture, but the methods are not limited thereto.

Additionally, the pH value of a culture may be adjusted while culturing by adding a compound such as ammonium hydroxide, potassium hydroxide, ammonia, phosphoric acid, and sulfuric acid to the culture in an appropriate manner. During the culture period, an antifoaming agent, such as fatty acid polyglycol ester, may be added to prevent foam generation. Additionally, oxygen or an oxygen-containing gas may be injected into the culture in order to maintain an aerobic state of the culture, or nitrogen, hydrogen, or carbon dioxide gas may be injected without the injection of a gas in order to maintain an anaerobic or microaerobic state of the culture. The culture temperature may generally be in the range from 27° C. to 37° C., and specifically, from 30° C. to 35° C. The culture may be continued until the desired amount of useful materials are obtained, and specifically for from 10 hours to 100 hours. L-amino acids may be released into the culture medium being cultured or may be contained in microorganisms.

Additionally, regarding the method of producing an L-amino acid of the present disclosure, the method of recovering the L-amino acid from a cultured microorganism or a culture is widely known in the art. The methods of recovering an L-amino acid may include filtration, anion exchange chromatography, crystallization, HPLC, etc., but are not limited thereto.

MODE FOR CARRYING OUT THE INVENTION

Hereinafter, the present disclosure will be described in more detail with reference to Examples. However, these Examples are for illustrative purposes only, and the disclosure is not intended to be limited by these Examples.

Example 1: Construction of a Library of E1p Variants by Artificial Mutagenesis

In this Example, a vector library for the primary cross insertion within the chromosome was constructed in order to obtain E1p variants by the method described below. Error-prone PCR was performed for the *Corynebacterium glutamicum* ATCC13032-derived aceE gene (SEQ ID NO: 2), which encodes E1p (SEQ ID NO: 1), and modified aceE gene (2852 bp) randomly introduced with base substitution were obtained. Error-prone PCR was performed by the Genemorph II Random Mutagenesis Kit (Stratagene) using *Corynebacterium glutamicum* ATCC13032 genomic DNA as a template along with primer 1 (SEQ ID NO: 3) and primer 2 (SEQ ID NO: 4).

```
primer 1 (SEQ ID NO: 3):
5'-TGGGA CCGGG AAACC GGG-3' primer 2 (SEQ ID NO: 4):
5'-GATTT ATCTG TCCCT TGA-3'
```

The amplified gene fragments were introduced with 0 to 3.5 base substitution per 1 kb, and PCR was performed for a total of 30 cycles under the following conditions: 96° C. denaturation for 30 sec, annealing at 53° C. for 30 sec, and polymerization at 72° C. for 2 min.

The amplified fragments were linked to pCR2.1-TOPO vector (hereinafter, "pCR2.1") using the pCR2.1-TOPO TA cloning kit (Invitrogen), transformed into *E. coli* DH5α, and plated on LB solid medium containing kanamycin (25 mg/L). The 20 different kinds of transformed colonies were selected and then plasmids were obtained therefrom. Upon analysis of the polynucleotide sequences of the plasmids, it was confirmed that modifications were introduced to mutually different positions with a frequency of 1.4 mutations/kb. About 20,000 transformed *E. coli* colonies were collected and their plasmids were extracted and named as "pCR2.1-aceE (mt)" library.

Additionally, a plasmid having the wild-type aceE gene to be used as the control strain was constructed. PCR was performed in the same manner as described above using the *Corynebacterium glutamicum* ATCC13032 genomic DNA as a template along with primer 1 (SEQ ID NO: 3) and primer 2 (SEQ ID NO: 4). For the polymerase, PfuUltra High-Fidelity DNA polymerase (Stratagene) was used and the thus-constructed plasmid was named as "pCR2.1-aceE (WT)."

Example 2: Construction of an aceE-Deletion Strain

An aceE-deletion strain was constructed for the introduction of the pCR2.1-aceE (mt) library using the KCCM11016P (the above microorganism was first published as KFCC10881 and re-deposited to an international depositary authority under the Budapest Treaty and assigned the Accession No. KCCM11016P; Korean Patent No. 10-0159812) strain as a parent strain.

For the construction of an aceE-deletion vector, PCR was performed using the chromosome of the wild-type *Corynebacterium glutamicum* ATCC13032 as a template along with primer 3 (SEQ ID NO: 5), primer 4 (SEQ ID NO: 6), primer 5 (SEQ ID NO: 7), and primer 6 (SEQ ID NO: 8).

```
primer 3 (SEQ ID NO: 5):
5'-GCAGG TCGAC TCTAG ATGCG ATTCG CGTCA
AACGT G-3' primer 4 (SEQ ID NO: 6):
5'-GTCCC TTGAG GTGAT GTGAA TCCAT CCACT-3' primer 5 (SEQ ID NO: 7):
5'-AGTGG ATGGA TTCAC ATCAC CTCAA GGGAC-3' primer 6 (SEQ ID NO: 8):
5'-CCGGG GATCC TCTAG ACGAA GCGCC GTGAG
CAATT C-3'
```

PCR was performed under the following conditions: denaturation at 95° C. for 5 min; 30 cycles of denaturation at 95° C. for 30 sec, annealing at 55° C. for 30 sec, and polymerization at 72° C. for 30 sec; and polymerization at 72° C. for 7 min.

As a result, SEQ ID NO: 9 (521 bp) and SEQ ID NO: 10 (538 bp), which respectively include the 5'terminus and 3'terminus, were obtained.

PCR was performed using the amplified sequences of SEQ ID NO: 9 and SEQ ID NO: 10 as templates along with primer 3 (SEQ ID NO: 5) and primer 6 (SEQ ID NO: 8).

PCR was performed under the following conditions: denaturation at 95° C. for 5 min; 30 cycles of denaturation at 95° C. for 30 sec, annealing at 55° C. for 30 sec, and polymerization at 72° C. for 60 sec; and polymerization at 72° C. for 7 min.

As a result, SEQ ID NO: 11 with a size of 1029 bp (hereinafter, ΔaceE), in which the 5' terminus and 3' terminus of the aceE gene were connected, was amplified.

The pDZ vector (Korean Patent No. 10-0924065), which cannot replicate in *Corynebacterium glutamicum*, and the ΔaceE fragment were treated with the restriction enzyme Xba I and ligated using a DNA ligase, and cloned to obtain a plasmid. The plasmid was named as pDZ-ΔaceE.

The pDZ-ΔaceE was transformed into *Corynebacterium glutamicum* KCCM11016P, which is a L-lysine producing strain, by electric pulse (*Appl. Microbiol. Biothcenol.* (1999) 52: 541-545), and the transformed strain was obtained from a selective medium containing kanamycin (25 mg/L). A strain, in which the aceE gene was inactivated by ΔaceE, the DNA fragment inserted into the genome via secondary cross-over, was obtained and named as KCCM11016PΔaceE.

Example 3: Construction of an E1p Artificial Variant Library and Screening of Strains with Enhanced Ability to Produce L-Lysine The constructed pCR2.1-aceE (mt) library, was transformed into the KCCM11016PΔaceE strain as a parent strain by homologous recombination, plated on a complex plate medium containing kanamycin (25 mg/L), and about 10,000 colonies were obtained, and each colony was named as "KCCM11016PΔaceE/pCR2.1-aceE(mt)-1" to "KCCM11016P/pCR2.1-aceE(mt)-10000," respectively.

Additionally, the thus-constructed pCR2.1-aceE (WT) vector was transformed into KCCM11016PΔaceE to obtain a control strain, and named as "KCCM11016PΔaceE/pCR2.1-aceE (WT)."

<Complex Plate Medium (pH 7.0)>

Glucose 10 g, Peptone 10 g, Beef Extract 5 g, Yeast Extract 5 g, Brain Heart Infusion 18.5 g, NaCl 2.5 g, Urea 2 g, Sorbitiol 91 g, and Agar 20 g (based on 1 L of distilled water)

The thus-obtained 10,000 colonies were respectively inoculated into a selective medium (300 μL) and cultured in 96-deep well plates maintained at 32° C. at a rate of 1000 rpm for about 24 hours. The amount of L-lysine production produced in the culture was analyzed by ninhydrin method (*J. Biol. Chem.* 1948. 176: 367-388). Upon completion of the culture, 10 μL of the culture supernatant and 190 μL of ninhydrin reaction solution were reacted at 65° C. for 30 minutes. The absorbance at wavelength 570 nm was measured by a spectrophotometer and was compared to that of the control strain KCCM11016PΔaceE/pCR2.1-aceE (WT), and 256 modified strains showing an absorbance with at least 10% increase were selected. Other colonies showed similar or reduced absorbance compared to that of the control strain.

<Selective Medium (pH 8.0)>

Glucose 10 g, $(NH_4)_2SO_4$ 5.5 g, $MgSO_4.7H_2O$ 1.2 g, $KH_2PO_4$ 0.8 g, $K_2HPO_4$ 16.4 g, Biotin 100 μg, Thiamine HCl 1000 μg, Calcium-Pantothenic Acid 2000 μg, and Nicotinamide 2000 μg (based on 1 L of distilled water)

The selected 256 strains were subjected to the ninhydrin reaction in the same manner as described above, and the top 53 kinds of strains with improved ability to produce L-lysine compared to that of KCCM11016PΔaceE/pCR2.1-aceE (WT) strain were selected.

Example 4: Confirmation of Abilities to Produce L-Lysine for Strains Selected from the E1p Artificial Variant Library For comparison of the abilities to produce L-lysine for the 53 different strains selected in Example 3, the strains were cultured by the method described below and the components of the cultures obtained thereof were analyzed.

Each of the strains was inoculated into 250 mL corner-baffle flasks containing 25 mL of a seed culture medium, respectively, and cultured in a shaking incubator (200 rpm)

at 30° C. for 20 hours. Each of the 250 mL corner-baffle flasks containing 24 mL of an L-lysine producing culture was inoculated with 1 mL of a seed culture liquid, and cultured in a shaking incubator (200 rpm) at 30° C. for 72 hours. The concentration of L-lysine in each culture was analyzed via HPLC.

<Seed Culture Medium (pH 7.0)>

Glucose (20 g), Peptone (10 g), Yeast Extract (5 g), Urea (1.5 g), $KH_2PO_4$ (4 g), $K_2HPO_4$ (8 g), $MgSO_4 \cdot 7H_2O$ (0.5 g), Biotin (100 μg), Thiamine HCl (1000 μg), Calcium-Pantothenic Acid (2000 μg), Nicotinamide (2000 μg) (based on 1 L of distilled water)

<Lysine-Producing Medium (pH 7.0)>

Glucose (100 g), $(NH_4)_2SO_4$ (40 g), Soybean Protein (2.5 g), Corn Steep Solids (5 g), Urea (3 g), $KH_2PO_4$ (1 g), $MgSO_4 \cdot 7H_2O$ (0.5 g), Biotin (100 μg), Thiamine HCl (1000 μg), Calcium-Pantothenic Acid (2000 μg), Nicotinamide (3000 μg), and $CaCO_3$ (30 g) (based on 1 L of distilled water)

The top 10 strains with highest L-lysine concentrations were selected from the 53 different strains, and the culture and the analysis described above were performed repeatedly. The L-lysine concentrations analyzed are shown in Table 1 below.

TABLE 1

Concentration of L-Lysine Produced by 10 Selected Strains KCCM11016PΔaceE/pCR2.1-aceE (mt)

|   | Strain | Batch 1 | Batch 2 | Batch 3 | Mean |
|---|---|---|---|---|---|
| Control | KCCM11016PΔaceE/pCR2.1-aceE (WT) | 42.1 | 41.9 | 41.7 | 41.9 |
| 1 | KCCM11016PΔaceE/pCR2.1-aceE (mt)-1235 | 45.1 | 46.2 | 45.8 | 45.7 |
| 2 | KCCM11016PΔaceE/pCR2.1-aceE (mt)-1542 | 45.6 | 46.1 | 44.9 | 45.5 |
| 3 | KCCM11016PΔaceE/pCR2.1-aceE (mt)-3152 | 46.1 | 45.7 | 46.0 | 45.9 |
| 4 | KCCM11016PΔaceE/pCR2.1-aceE (mt)-5013 | 44.5 | 45.1 | 45.7 | 45.1 |
| 5 | KCCM11016PΔaceE/pCR2.1-aceE (mt)-5312 | 45.9 | 44.9 | 46.1 | 45.6 |
| 6 | KCCM11016PΔaceE/pCR2.1-aceE (mt)-6001 | 44.8 | 45.7 | 45.4 | 45.3 |
| 7 | KCCM11016PΔaceE/pCR2.1-aceE (mt)-7139 | 46.1 | 46.3 | 45.9 | 46.1 |
| 8 | KCCM11016PΔaceE/pCR2.1-aceE (mt)-8264 | 46.6 | 48.1 | 47.3 | 47.3 |
| 9 | KCCM11016PΔaceE/pCR2.1-aceE (mt)-9174 | 45.6 | 45.1 | 44.8 | 45.2 |
| 10 | KCCM11016PΔaceE/pCR2.1-aceE (mt)-9586 | 46.1 | 46.6 | 45.9 | 46.2 |

As a result of the analysis of L-lysine concentration, it was confirmed that the L-lysine yield of the 10 selected strains showed a maximum increase of 22% compared to the control strain, KCCM11016PΔaceE/pCR2.1-aceE (WT) strain.

Example 5: Confirmation of aceE Gene Modification of Strains Selected from the E1p Artificial Variant Library In order to confirm the substitutions introduced in E1p of the 10 strains selected in Example 4, the polynucleotide sequences of modified aceE were analyzed. To determine the polynucleotide sequences, PCR was performed using primer 1 (SEQ ID NO: 3) and primer 2 (SEQ ID NO: 4).

```
primer 1 (SEQ ID NO: 3):
5'-TGGGA CCGGG AAACC GGG-3' primer 2 (SEQ ID NO: 4):
5'-GATTT ATCTG TCCCT TGA-3'
```

The polynucleotide sequences of each of the modified-type of aceE gene fragments obtained were confirmed by analysis, and compared with the polynucleotide sequence of SEQ ID NO: 2, and thus the amino acid sequences of the E1p variants were confirmed. The information on the substitutions of the E1p amino acid sequences of the selected strains is shown in Table 2 below.

TABLE 2

E1p Amino Acid Substitution of KCCM11016P/pCR2.1-aceE (mt) of 10 Selected Strains

| Strain | E1p Amino Acid Substitution |
|---|---|
| KCCM11016PΔaceE/pCR2.1-aceE (mt)-1235 | Q432E |
| KCCM11016PΔaceE/pCR2.1-aceE (mt)-1542 | E190V |
| KCCM11016PΔaceE/pCR2.1-aceE (mt)-3152 | L438P |
| KCCM11016PΔaceE/pCR2.1-aceE (mt)-5013 | Q195H |
| KCCM11016PΔaceE/pCR2.1-aceE (mt)-5312 | P199S |
| KCCM11016PΔaceE/pCR2.1-aceE (mt)-6001 | K435A |
| KCCM11016PΔaceE/pCR2.1-aceE (mt)-7139 | Q432A |
| KCCM11016PΔaceE/pCR2.1-aceE (mt)-8264 | Y418H |
| KCCM11016PΔaceE/pCR2.1-aceE (mt)-9174 | N428A |
| KCCM11016PΔaceE/pCR2.1-aceE (mt)-9586 | Y201A |

Example 6: Construction of a Vector for Introducing the E1p Variant on Chromosome In order to confirm the application effect of the E1p variant confirmed in Example 5, a vector for introducing the same on the chromosome was constructed.

The primer 9 (SEQ ID NO: 12), which is introduced with an Xba I restriction site at 5' terminus, and the primer 10 (SEQ ID NO: 13), which is introduced with an Xba I restriction site at 3' terminus, were synthesized based on the reported polynucleotide sequences. The aceE (mt) gene fragments of 10 different modified-type of strains were amplified by PCR using the chromosomes of the selected 10 different strains as templates, respectively.

PCR was performed under the following conditions: denaturation at 94° C. for 5 min; 30 cycles of denaturation at 94° C. for 30 sec, annealing at 56° C. for 30 sec, and polymerization at 72° C. for 2 min; and polymerization at 72° C. for 7 min.

```
primer 9 (SEQ ID NO: 12):
5'-AATCT AGATG GGACC GGGAA ACCGG G-3' primer 10 (SEQ ID NO: 13):
5'-AATCT AGAGA TTTAT CTGTC CCTTG A-3'
```

The PCR-amplified gene fragments of the 10 different strains were treated with Xba I to obtain the respective DNA fragments thereof, and the fragments were linked to the pDZ vector for introducing chromosomes including an Xba I restriction site, transformed into E. coli DH5α, and streaked on solid LB medium containing kanamycin (25 mg/L).

The transformed colonies transformed with a vector inserted with a target gene were selected by PCR and the plasmids were obtained by the conventionally known plasmid extraction method. According to the modification inserted in E1p of each plasmid, the plasmids were named as pDZ-E1p (Q432E), pDZ-E1p (E190V), pDZ-E1p (L438P), pDZ-E1p (Q195H), pDZ-E1p (P199S), pDZ-E1p (K435A), pDZ-E1p (Q432A), pDZ-E1p (Y418H), pDZ-E1p (N428A), and pDZ-E1p (Y201A), respectively.

Example 7: Construction of a KCCM11016P-Derived Strain Introduced with the E1p Variant and Comparison of their Abilities to Produce L-Lysine

*Corynebacterium glutamicum* KCCM11016P, an L-lysine producing strain, was transformed by a 2-step recombination of homologous chromosomes using the 10 vectors for introducing the Novel E1p variant prepared in Example 6. Then, the strains introduced with the E1p variant on the chromosomes were selected by analyzing the polynucleotide sequences, and the plasmids were named as KCCM11016P:: E1p (Q432E), KCCM11016P::E1p (E190V), KCCM11016P::E1p (L438P), KCCM11016P::E1p (Q195H), KCCM11016P::E1p (P199S), KCCM11016P:: E1p (K435A), KCCM11016P::E1p (Q432A), KCCM11016P::E1p (Y418H), KCCM11016P::E1p (N428A), and KCCM11016P::E1p (Y201A) according to the inserted E1p variant, respectively.

The strains were cultured in the same manner as in Example 4, and the L-lysine concentrations of the cultures were analyzed. For the measurement of the growth rate of the constructed strains, the residual glucose concentration of the cultures was measured 18 hours after the initiation of the culture (Table 3).

glucose consumption rate while showing a maximum increase of 10% in lysine production, compared to those of the parent strain.

In this regard, the present inventors named KCCM11016P::E1p (N428A), the representative strain among the strains with improved ability to produce L-lysine, as *Corynebacterium glutamicum* "CA01-2289," and deposited the strain with the Korean Culture Center of Microorganisms, recognized as an international depositary authority under the Budapest Treaty, on Oct. 23, 2014, under the accession number KCCM11590P.

Upon examination, it was confirmed that the E1p variants of the 10 different strains (i.e., E1p (Q432E) (SEQ ID NO: 14), E1p (E190V) (SEQ ID NO: 15), E1p (L438P) (SEQ ID NO: 16), E1p (Q195H) (SEQ ID NO: 17), E1p (P199S) (SEQ ID NO: 18), E1p (K435A) (SEQ ID NO: 19), E1p (Q432A) (SEQ ID NO: 20), E1p (Y418H) (SEQ ID NO: 21), E1p (Y201A) (SEQ ID NO: 22), and E1p (N428A) (SEQ ID NO: 23)) were heavily distributed in two groups (amino acid residues at positions from 190 to 201, and amino acids at positions from 418 to 438).

Ten different strains, in which substitutions belonging to each group were included in combination, (i.e., (KCCM11016P::E1p (E190V, Q195H) (SEQ ID NO:24), KCCM11016P::E1p (E190V, P199S) (SEQ ID NO:25), KCCM11016P::E1p (Q195H, P199S) (SEQ ID NO:26), KCCM11016P::E1p (E190V, Y201A) (SEQ ID NO:27), KCCM11016P::E1p (Q195H, Y201A) (SEQ ID NO:28), KCCM11016P::E1p (P199S, Y201A) (SEQ ID NO:29),

TABLE 3

Concentration (g/L) of Residual Glucose and L-Lysine Produced by KCCM11016P-Derived Strains Introduced with the E1p variant

| | | Batch 1 | | Batch 2 | | Batch 3 | | Mean | |
|---|---|---|---|---|---|---|---|---|---|
| | Strain | residual glucose | L-lysine | residual glucose | L-lysine | residual glucose | L-lysine | residual glucose | L-lysine |
| Control | KCCM11016P | 35.8 | 42.8 | 34.5 | 41.6 | 35.1 | 43.1 | 35.1 | 42.5 |
| 1 | KCCM11016P::E1p (Q432E) | 41.2 | 46.2 | 40.5 | 45.8 | 42.1 | 45.2 | 41.3 | 45.7 |
| 2 | KCCM11016P::E1p (E190V) | 43.2 | 45.2 | 41.8 | 45.8 | 43 | 46.7 | 42.7 | 45.9 |
| 3 | KCCM11016P::E1p (L438P) | 40.5 | 45.1 | 41.1 | 45.9 | 40.6 | 45.8 | 40.7 | 45.6 |
| 4 | KCCM11016P::E1p (Q195H) | 38.1 | 44.5 | 37.5 | 45.2 | 38.5 | 44.9 | 38.0 | 44.9 |
| 5 | KCCM11016P::E1p (P199S) | 44.1 | 46.2 | 43.5 | 45.9 | 44.8 | 44.8 | 43.8 | 45.6 |
| 6 | KCCM11016P::E1p (K435A) | 44.1 | 45.2 | 43.5 | 45.1 | 42.9 | 46.5 | 43.5 | 45.6 |
| 7 | KCCM11016P::E1p (Q432A) | 40.5 | 46.5 | 38.9 | 46.1 | 40.3 | 45.8 | 39.9 | 46.1 |
| 8 | KCCM11016P::E1p (Y418H) | 38.5 | 47.5 | 37.6 | 46.6 | 39.1 | 46.5 | 38.4 | 46.9 |
| 9 | KCCM11016P::E1p (Y201A) | 42.5 | 45.7 | 43.1 | 44.6 | 40.5 | 45.8 | 42.0 | 45.4 |
| 10 | KCCM11016P::E1p (N428A) | 39.8 | 46.5 | 40.1 | 47.9 | 40.3 | 46.2 | 40.1 | 46.9 |

The novel 10 different strains (i.e., KCCM11016P::E1p (Q432E), KCCM11016P::E1p (E190V), KCCM11016P:: E1p (L438P), KCCM11016P::E1p (Q195H), KCCM11016P::E1p (P199S), KCCM11016P::E1p (K435A), KCCM11016P::E1p (Q432A), KCCM11016P:: E1p (Y418H), KCCM11016P::E1p (Y201A), and KCCM11016P::E1p (N428A)), showed a slight decrease in KCCM11016P::E1p (N428A, Q432E) (SEQ ID NO:30), KCCM11016P::E1p (N428A, K435A) (SEQ ID NO:31), KCCM11016P::E1p (Y418H, K435A) (SEQ ID NO:32), KCCM11016P::E1p (Y418H, Q432A) (SEQ ID NO:33)) were synthesized, and their abilities to produce L-lysine were measured in the same manner as described above (Table 4).

TABLE 4

Concentration (g/L) of Residual Glucose and L-Lysine Produced by KCCM11016P-Derived Strains Introduced with Combination of E1p substitutions

|   | Strain | Batch 1 | | Batch 2 | | Batch 3 | | Mean | |
|---|---|---|---|---|---|---|---|---|---|
|   |   | residual glucose | L-lysine | residual glucose | L-lysine | residual glucose | L-lysine | residual glucose | L-lysine |
| Control | KCCM11016P | 35.2 | 42.1 | 34.6 | 42.5 | 35.6 | 42.5 | 35.1 | 42.4 |
| 1 | KCCM11016P::E1p (E190V, Q195H) | 47.1 | 47.1 | 46.5 | 48.1 | 46 | 43.1 | 46.5 | 46.1 |
| 2 | KCCM11016P::E1p (E190V, P199S) | 45.2 | 45.2 | 46.3 | 46.1 | 46 | 45 | 45.8 | 45.4 |
| 3 | KCCM11016P::E1p (Q195H, P199S) | 46.2 | 49.8 | 45.7 | 48.7 | 44 | 48.5 | 45.3 | 49.0 |
| 4 | KCCM11016P::E1p (E190V, Y201A) | 42.8 | 46.1 | 43.1 | 45.7 | 42.5 | 46 | 42.8 | 45.9 |
| 5 | KCCM11016P::E1p (Q195H, Y201A) | 48.3 | 45.3 | 47.5 | 47.1 | 47 | 46.2 | 47.6 | 46.2 |
| 6 | KCCM11016P::E1p (P199S, Y201A) | 39.1 | 45.3 | 38.6 | 45.9 | 39.2 | 45.6 | 39.0 | 45.6 |
| 7 | KCCM11016P::E1p (N428A, Q432E) | 45.9 | 48.1 | 47.1 | 49.2 | 46.5 | 49.3 | 46.5 | 48.9 |
| 8 | KCCM11016P::E1p (N428A, K435A) | 46.1 | 47.9 | 45.8 | 48.3 | 46.7 | 47.9 | 46.2 | 48.0 |
| 9 | KCCM11016P::E1p (Y418H, K435A) | 38.2 | 45.9 | 37.6 | 45.7 | 39.1 | 46 | 38.3 | 45.9 |
| 10 | KCCM11016P::E1p (Y418H, Q432A) | 41.2 | 46.1 | 40.9 | 45.1 | 39.9 | 47.2 | 40.7 | 46.1 |

As shown in Table above, all of the novel 10 strains with combined substitutions showed a slight decrease in glucose consumption rate while showing a maximum increase of 15.6% in the ability to produce L-lysine. The results confirm that a strain which is introduced with a combined substitution can exhibit improved ability to produce L-lysine than a strain which is introduced with single novel substitution.

The results confirm that the 10 strains with novel variants of E1p protein are effective strains which can significantly increasing an ability to produce L-lysine while not significantly reducing glucose consumption rate, compared to that of the parent strain, and also confirm that the amino acid residues at positions from 190 to 205, or from 415 to 440 are major regions that can exhibit the effects described above.

Example 8: Measurement of Activity of Pyruvate Dehydrogenase Complex (PDHC) Regarding Strains Introduced with the E1p Variant The PDHC activity was measured regarding the selected strains by the method reported in the previous journal (Schreiner et al., *J. Bacteriol.* 187:6005, 2005). The control strains KCCM11016P and KCCM11016PΔaceE, and the 10 selected strains (KCCM11016P::E1p (Q432E), KCCM11016P::E1p (E190V), KCCM11016P::E1p (L438P), KCCM11016P::E1p (Q195H), KCCM11016P:: E1p (P199S), KCCM11016P::E1p (K435A), KCCM11016P::E1p (Q432A), KCCM11016P::E1p (Y418H), KCCM11016P::E1p (Y201A), and KCCM11016P::E1p (N428A)), were inoculated into 25 mL of the seed culture medium specified in Example 4, and cultured until the late logarithmic phase.

The cells were collected by centrifugation and washed twice with 100 mM Tris-HCl (pH 7.2, 3 mM L-cysteine, 10 mM MgCl$_2$) buffer solution, and finally suspended in 2 mL of the same buffer solution. The suspension of the cells was physically crushed by the general glass bead vortexing method for 10 minutes, and the supernatant was recovered by performing centrifugation (13,000 rpm, 4° C., and 30 min) twice and used as a crude extract for the measurement of the activity of PDHC enzyme. For the measurement of the activity of PDHC enzyme, a reaction solution (10 mM MgCl$_2$, 3 mM cysteine, 2 mM NAD, 0.9 mM thiamine diphosphate, 0.25 mM chlorpromazine, 6 mM pyruvate, 0.2 mM CoA in Tris-HCl buffer (pH 7.2)) for measuring the enzyme activity in an amount of 0.95 mL was added with 0.05 mL of the crude extract, and reacted at 30° C. The activity unit of PDHC was defined in terms of NADH μmoles consumed per minute, and the measurement results of the enzyme activity are shown in Table 5 below.

TABLE 5

Measurement of Enzyme Activity of PDHC (%)

| Strain | PDHC Activity (%) |
|---|---|
| KCCM11016P | 100 |
| KCCM11016PΔaceE | 0 |
| KCCM11016P::E1p (Q432E) | 39 |
| KCCM11016P::E1p (E190V) | 56 |
| KCCM11016P::E1p (L438P) | 53 |
| KCCM11016P::E1p (Q195H) | 55 |
| KCCM11016P::E1p (P199S) | 51 |
| KCCM11016P::E1p (K435A) | 53 |
| KCCM11016P::E1p (Q432A) | 42 |
| KCCM11016P::E1p (Y418H) | 36 |
| KCCM11016P::E1p (Y201A) | 46 |
| KCCM11016P::E1p (N428A) | 35 |

The PDHC activity of the strains introduced with novel variants showed the activity of 35% to 56% relative to the parent strain.

Example 9: Comparison of an Ability to Produce L-Lysine with aceE-Deletion Strain For the comparative evaluation of KCCM11016PΔaceE, the aceE-deletion strain constructed in Example 2, and the 10 selected strains (KCCM11016P::E1p (Q432E), KCCM11016P::E1p (E190V), KCCM11016P::E1p (L438P), KCCM11016P::E1p (Q195H), KCCM11016P::E1p (P199S), KCCM11016P::E1p (K435A), KCCM11016P::E1p (Q432A), KCCM11016P::E1p (Y418H), KCCM11016P::E1p (Y201A), and KCCM11016P::E1p (N428A)), the strains were cultured in the same manner as in Example 4 using media containing ammonium acetate. The L-lysine concentration of the resulting cultures was analyzed by HPLC, and for the measurement of the growth rate of the constructed strains, the concentration of the residual glucose was measured 18 hours after the initiation of the culture (Table 6).

<Lysine-Producing Medium Containing Ammonium Acetate (pH 7.0)>

Glucose (100 g), $CH_3COONH_3$ (5 g), $(NH_4)_2SO_4$ (40 g), Soybean Protein (2.5 g), Corn Steep Solids (5 g), Urea (3 g), $KH_2PO_4$ (1 g), $MgSO_4.7H_2O$ (0.5 g), Biotin (100 μg), Thiamine HCl (1000 μg), Calcium-Pantothenic Acid (2000 μg), Nicotinamide (3000 μg), and $CaCO_3$ (30 g) (based on 1 L of distilled water)

glutamicum, strains in which each of the 10 different E1p variants was respectively introduced into *Corynebacterium glutamicum* KFCC10750 (the above microorganism was first published as KFCC10750 and re-deposited to an international depositary authority under the Budapest Treaty and assigned the Accession No. KCCM11347P; Korean Patent No. 10-0073610), an L-lysine producing strain, were constructed in the same manner as in Example 7, and the strains were named as KFCC10750::E1p (Q432E), KFCC10750::E1p (E190V), KFCC10750::E1p (L438P), KFCC10750::E1p (Q195H), KFCC10750::E1p (P1998), KFCC10750::E1p (K435A), KFCC10750::E1p (Q432A), KFCC10750::E1p (Y418H), KFCC10750::E1p (Y201A), and KFCC10750::E1p (N428A). The eleven strains including the KFCC10750 strain as the control strain were cultured in the same manner as in Example 4, and the L-lysine concentration of the cultures of the strains was analyzed (Table 7).

TABLE 6

Concentration (g/L) of Residual Glucose and L-Lysine Produced by KCCM11016P-Derived Strains Introduced with E1p Variants and aceE-Deletion Strains

| | | Batch 1 | | Batch 2 | | Batch 3 | | Mean | |
|---|---|---|---|---|---|---|---|---|---|
| | Strain | residual glucose | L-lysine | residual glucose | L-lysine | residual glucose | L-lysine | residual glucose | L-lysine |
| Control | KCCM11016P | 45.7 | 40.9 | 45.6 | 42.1 | 46.7 | 41.3 | 46.0 | 41.4 |
| Experimental Group | KCCM11016PΔaceE | 67.1 | 45.6 | 66.8 | 45.2 | 68.2 | 45.4 | 67.4 | 45.4 |
| 1 | KCCM11016P::E1p (Q432E) | 48.2 | 43.7 | 46.5 | 44.2 | 47.5 | 43.4 | 47.4 | 43.8 |
| 2 | KCCM11016P::E1p (E190V) | 49.7 | 44.6 | 47.8 | 43.8 | 48.1 | 44.4 | 48.5 | 44.3 |
| 3 | KCCM11016P::E1p (L438P) | 47.9 | 45.3 | 48.9 | 43.2 | 47.5 | 44.6 | 48.1 | 44.4 |
| 4 | KCCM11016P::E1p (Q195H) | 46.7 | 42.9 | 46.3 | 43.6 | 45.6 | 43.0 | 46.2 | 43.2 |
| 5 | KCCM11016P::E1p (P199S) | 50.4 | 45.2 | 50.6 | 45.1 | 51.2 | 44.6 | 50.7 | 45.0 |
| 6 | KCCM11016P::E1p (K435A) | 51.3 | 44.9 | 50.9 | 45.2 | 52.7 | 45.0 | 51.6 | 45.0 |
| 7 | KCCM11016P::E1p (Q432A) | 48.9 | 45.6 | 47.8 | 46.0 | 47.9 | 45.9 | 48.2 | 45.8 |
| 8 | KCCM11016P::E1p (Y418H) | 44.6 | 45.8 | 45.7 | 46.5 | 47.3 | 46.3 | 45.9 | 46.2 |
| 9 | KCCM11016P::E1p (Y201A) | 47.6 | 43.8 | 46.7 | 44.5 | 48.7 | 43.7 | 47.7 | 44.0 |
| 10 | KCCM11016P::E1p (N428A) | 49.7 | 46.2 | 47.8 | 45.2 | 48.3 | 45.7 | 48.6 | 45.7 |

The KCCM11016PΔaceE strain showed an increase of 9.6% in the ability to produce L-lysine but a significantly reduced growth rate, compared to the parent strain. In contrast, the strains introduced with substitutions showed an increase in lysine yield and glucose consumption rate similar to when ammonium acetate was not added.

The results indicate that the strain introduced with the aceE variants can produce lysine in high yield without a noticeable effect in growth rate, compared to the aceE-deletion strain which can increase lysine yield with a significant decrease in growth rate.

Example 10: Construction of KFCC10750-Derived Strains Introduced with the E1p Variant and Comparison of their Abilities to Produce L-Lysine For confirming the effects of introduction of 10 novel variants in other strains of the genus *Corynebacterium*

TABLE 7

Concentration of L-Lysine Produced by KCCM10750P-Derived Strains Introduced with The E1p variant

| | | L-Lysine (g/L) | | | |
|---|---|---|---|---|---|
| | Strain | Batch 1 | Batch 2 | Batch 3 | Mean |
| Control | KFCC10750 | 38.8 | 38.1 | 37.9 | 38.3 |
| 1 | KFCC10750::E1p (Q432E) | 43.1 | 42.8 | 43.5 | 43.1 |
| 2 | KFCC10750::E1p (E190V) | 41.2 | 42.1 | 41.8 | 41.7 |
| 3 | KFCC10750::E1p (L438P) | 40.9 | 41.3 | 41.5 | 41.2 |
| 4 | KFCC10750:E1p (Q195H) | 41.6 | 42.3 | 41.8 | 41.9 |
| 5 | KFCC10750::E1p (P199S) | 42 | 42.4 | 41.9 | 42.1 |
| 6 | KFCC10750::E1p (K435A) | 41.8 | 42.1 | 42.2 | 42.0 |
| 7 | KFCC10750::E1p (Q432A) | 40.2 | 41.1 | 41.2 | 40.8 |
| 8 | KFCC10750::E1p (Y418H) | 44.5 | 44.9 | 44.8 | 44.7 |
| 9 | KFCC10750::E1p (Y201A) | 40.9 | 41 | 41.1 | 41.0 |
| 10 | KFCC10750::E1p (N428A) | 44.5 | 44.1 | 45.8 | 44.8 |

As a result, it was confirmed that the 10 different strains introduced with novel variants had a maximum increase of 17% of the ability to produce L-lysine compared to the parent strain.

Example 11: Construction of KCCM10770P-Derived Strains Introduced with the E1p Variant and Comparison of their Abilities to Produce L-Lysine For confirming the effects of introduction of 10 novel variants in other strains of the genus *Corynebacterium glutamicum*, strains in which each E1p variant was introduced into *Corynebacterium glutamicum* KCCM10770P (Korean Patent No. 10-0924065), an L-lysine producing strain, were constructed in the same manner as in Example 7, and the strains were named as KCCM10770P::E1p (Q432E), KCCM10770P::E1p (E190V), KCCM10770P::E1p (L438P), KCCM10770P::E1p (Q195H), KCCM10770P::E1p (P199S), KCCM10770P::E1p (K435A), KCCM10770P::E1p (Q432A), KCCM10770P::E1p (Y418H), KCCM10770P::E1p (Y201A), and KCCM10770P::E1p (N428A). The strains including the KFCC10750 strain as the control strain were cultured in the same manner as in Example 4, and the L-lysine concentration of the cultures of the strains was analyzed (Table 8).

TABLE 8

Concentration of L-Lysine Produced by KCCM10770P-Derived Strains Introduced with the E1p variant

| | | L-Lysine (g/L) | | | |
|---|---|---|---|---|---|
| | Strain | Batch 1 | Batch 2 | Batch 3 | Mean |
| Control | KCCM10770P | 48.1 | 47.5 | 47.8 | 47.8 |
| 1 | KCCM10770P::E1p (Q432E) | 53.3 | 53.4 | 54.1 | 53.6 |
| 2 | KCCM10770P::E1p (E190V) | 51.2 | 52.1 | 52.8 | 52.0 |
| 3 | KCCM10770P::E1p (L438P) | 51.5 | 51.3 | 50.7 | 51.2 |
| 4 | KCCM10770P::E1p (Q195H) | 51.9 | 52.1 | 52 | 52.0 |
| 5 | KCCM10770P::E1p (P199S) | 51.3 | 52.1 | 52.7 | 52.0 |
| 6 | KCCM10770P::E1p (K435A) | 52.4 | 52.6 | 51.4 | 52.1 |
| 7 | KCCM10770P::E1p (Q432A) | 50.2 | 51.2 | 50 | 50.5 |
| 8 | KCCM10770P::E1p (Y418H) | 55.8 | 54.5 | 54.1 | 54.8 |
| 9 | KCCM10770P::E1p (Y201A) | 49.9 | 50.3 | 50.7 | 50.3 |
| 10 | KCCM10770P::E1p(N428A) | 56.1 | 55.7 | 55.9 | 55.9 |

As a result, it was confirmed that the 10 strains introduced with novel variants had a maximum increase of 17% of the ability to produce L-lysine compared to the parent strain.

Example 12: Construction of CJ3P-Derived Strains Introduced with the E1p Variant and Comparison of their Abilities to Produce L-Lysine For confirming the effects of introduction of E1p variants in other strains of the genus *Corynebacterium glutamicum*, strains in which each E1p variant was introduced into *Corynebacterium glutamicum* CJ3P (Binder et al., Genome Biology 2012, 13: R40), an L-lysine producing strain, were constructed in the same manner as in Example 7, and the strains were named as CJ3P::E1p (Q432E), CJ3P::E1p (E190V), CJ3P::E1p (L438P), CJ3P::E1p (Q195H), CJ3P::E1p (P199S), CJ3P::E1p (K435A), CJ3P::E1p (Q432A), CJ3P::E1p (Y418H), CJ3P::E1p (Y201A), and CJ3P::E1p (N428A). The strains were cultured in the same manner as in Example 4, and the L-lysine concentration of the cultures of the strains was analyzed (Table 9).

TABLE 9

Concentration of L-Lysine Produced by CJ3P-Derived Strains Introduced with the E1p variant

| | | L-Lysine (g/L) | | | |
|---|---|---|---|---|---|
| | Strain | Batch 1 | Batch 2 | Batch 3 | Mean |
| Control | CJ3P | 8.2 | 8.3 | 8 | 8.2 |
| 1 | CJ3P::E1p (Q432E) | 9.5 | 9.3 | 9.4 | 9.4 |
| 2 | CJ3P::E1p (E190V) | 8.8 | 9 | 8.7 | 8.8 |
| 3 | CJ3P::E1p (L438P) | 9.1 | 8.7 | 8.9 | 8.9 |
| 4 | CJ3P::E1p (Q195H) | 9.2 | 8.9 | 9 | 9.0 |
| 5 | CJ3P::E1p (P199S) | 9.3 | 9 | 9.1 | 9.1 |
| 6 | CJ3P::E1p (K435A) | 9.1 | 9 | 8.9 | 9.0 |
| 7 | CJ3P::E1p (Q432A) | 8.7 | 8.9 | 8.8 | 8.8 |
| 8 | CJ3P::E1p (Y418H) | 9.6 | 9.6 | 9.5 | 9.6 |
| 9 | CJ3P::E1p (Y201A) | 8.7 | 8.7 | 8.9 | 8.8 |
| 10 | CJ3P::E1p (N428A) | 9.7 | 9.8 | 9.8 | 9.8 |

As a result, it was confirmed that the 10 different strains introduced with novel variants had a maximum increase of 19.5% of the ability to produce L-lysine, compared to the parent strain.

The results indicate that each of the newly obtained 10 different strains with the E1p variant (E1p (Q432E), E1p (E190V), E1p (L438P), E1p (Q195H), E1p (P199S), E1p (K435A), E1p (Q432A), E1p (Y418H), E1p (Y201A), and E1p (N428A)) has excellent effect of increasing the ability to produce L-lysine, respectively.

Example 13: Construction of KCCM11201P-Derived Strains Introduced with the E1p Variant and Comparison of their Abilities to Produce L-Valine For confirming the effects of the 10 selected strains with E1p variants in other amino acids-producing strains of the genus *Corynebacterium glutamicum*, strains in which the E1p variant was introduced into *Corynebacterium glutamicum* KFCC11201P (Korean Patent No. 10-1117022), an L-valine producing strain, were constructed in the same manner as in Example 7, and the strains were named as KCCM11201P::E1p (Q432E), KCCM11201P::E1p (E190V), KCCM11201P::E1p (L438P), KCCM11201P::E1p (Q195H), KCCM11201P::E1p (P199S), KCCM11201P::E1p (K435A), KCCM11201P::E1p (Q432A), KCCM11201P::E1p (Y418H), KCCM11201P::E1p (Y201A), and KCCM11201P::E1p (N428A).

For the evaluation of the strains, each of the strains was inoculated into 250 mL corner-baffle flasks containing 25 mL of L-valine specified below, respectively, and cultured in a shaking incubator (200 rpm) at 30° C. for 20 hours. The L-valine concentration in each culture was analyzed via HPLC (Table 10).

<Valine-Producing Medium (pH 7.2)>

Glucose (50 g), $(NH_4)_2SO_4$ (20 g), Corn Steep liquid (20 g), $KH_2PO_4$ (1 g), $MgSO_4 \cdot 7H_2O$ (0.5 g), Biotin (200 μg), and $CaCO_3$ (30 g) (based on 1 L of distilled water)

TABLE 10

Concentration of L-valine Produced by KCCM11201P-Derived Strains Introduced with the E1p variant

| | | L-valine (g/L) | | |
|---|---|---|---|---|
| | Strain | Batch 1 | Batch 2 | Mean |
| Control | KCCM11201P | 2.8 | 2.8 | 2.8 |
| 1 | KCCM11201P::E1p (Q432E) | 3.1 | 3.0 | 3.1 |
| 2 | KCCM11201P::E1p (E190V) | 3.3 | 3.2 | 3.3 |
| 3 | KCCM11201P::E1p (L438P) | 3.2 | 3.2 | 3.2 |
| 4 | KCCM11201P::E1p (Q195H) | 3.0 | 3.1 | 3.1 |
| 5 | KCCM11201P::E1p (P199S) | 3.1 | 3.3 | 3.2 |
| 6 | KCCM11201P::E1p (K435A) | 3.1 | 3.1 | 3.1 |
| 7 | KCCM11201P::E1p (Q432A) | 3.2 | 3.2 | 3.2 |
| 8 | KCCM11201P::E1p (Y418H) | 3.3 | 3.4 | 3.4 |
| 9 | KCCM11201P::E1p (Y201A) | 3.0 | 3.0 | 3.0 |
| 10 | KCCM11201P::E1p (N428A) | 3.4 | 3.4 | 3.4 |

As a result, it was confirmed that the 10 different strains introduced with novel variants had a maximum increase of 21% of the ability to produce L-valine, compared to the parent strain.

Example 14: Construction of Wild Type-Derived Strains Introduced with the E1p Variant and Comparison of their Abilities to Produce L-Valine For reconfirming the ability to produce L-valine for the four different variants, among the 10 selected E1p variants, which showed the effect of a high increase in L-valine yield, strains in which each E1p variant was introduced into *Corynebacterium glutamicum* ATCC13032 were constructed in the same manner as in Example 7, and the strains were named as ATCC13032::E1p (E190V), ATCC13032::E1p (L438P), ATCC13032::E1p (Y418H), and ATCC13032::E1p (N428A).

For confirming the ability to produce L-valine for the above strains, each of the strains was transformed with pECCG117-DvalS (Korean Patent Application Publication No. 10-2014-0111421), which is an overexpression vector for L-valine biosynthesis, by electroporation. The transformed strains were obtained from selective media containing kanamycin (25 mg/L) and named as ATCC13032::E1p (E190V)_DvalS, ATCC13032::E1p (L438P)_DvalS, ATCC13032::E1p (Y418H)_DvalS, and ATCC13032::E1p (N428A)_DvalS.

The strains were cultured in the same manner as in Example 13 and the concentration of L-valine in each culture was analyzed (Table 11).

TABLE 11

Concentration of L-valine Produced by Wild Type-Derived Strains Introduced with the E1p variant

| | | L-valine (g/L) | | |
|---|---|---|---|---|
| | Strain | Batch 1 | Batch 2 | Mean |
| | ATCC13032 | 0.1 | 0.1 | 0.1 |
| Control | ATCC13032_DvalS | 1.3 | 1.2 | 1.3 |
| 1 | ATCC13032::E1p (E190V) | 0.1 | 0.1 | 0.1 |
| 2 | ATCC13032::E1p (E190V)_DvalS | 1.5 | 1.7 | 1.6 |
| 3 | ATCC13032::E1p (L438P) | 0.1 | 0.1 | 0.1 |
| 4 | ATCC13032::E1p (L438P)_DvalS | 1.4 | 1.4 | 1.4 |
| 5 | ATCC13032::E1p (Y418H) | 0.1 | 0.1 | 0.1 |
| 6 | ATCC13032::E1p (Y418H)_DvalS | 1.8 | 1.7 | 1.8 |
| 7 | ATCC13032::E1p (N428A) | 0.1 | 0.1 | 0.1 |
| 8 | ATCC13032::E1p (N428A)_DvalS | 1.9 | 1.7 | 1.8 |

As a result, it was confirmed that the four different strains introduced with novel variants had a maximum increase of 38% of the ability to produce L-valine, compared to the control strain.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A polypeptide having pyruvate dehydrogenase activity, wherein the polypeptide comprises an amino acid sequence having at least 95% sequence identity to the amino acid sequence of SEQ ID NO: 1, and wherein at least one of the amino acids at the positions corresponding to positions 418, 428, 432, 435, and 438 of SEQ ID NO: 1 is substituted with a different amino acid in the amino acid sequence of the polypeptide.

2. The polypeptide of claim 1, wherein the substitution is selected from the group consisting of a substitution at position 418 from tyrosine to histidine (Y418H), a substitution at position 428 from asparagine to alanine (N428A), a substitution at position 432 from glutamine to glutamic acid (Q432E), a substitution at position 432 from glutamine to alanine (Q432A), a substitution at position 435 from lysine to alanine (K435A), and a substitution at position 438 from leucine to proline (L438P).

3. The polypeptide of claim 1, wherein the amino acid sequence of the polypeptide is selected from the group consisting of SEQ ID NO: 14, 16, 19, 20, 21, 23, 30, 31, 32, and 33.

4. A polynucleotide comprising a nucleotide sequence encoding the polypeptide of claim 1.

5. A microorganism of the genus *Corynebacterium* producing an L-amino acid, wherein the microorganism comprises the polypeptide of claim 1.

6. The microorganism of claim 5, wherein the microorganism is *Corynebacterium glutamicum*.

7. A method for producing an L-amino acid, comprising:
(a) culturing the microorganism of claim 5 in a medium to produce an L-amino acid; and
(b) recovering the L-amino acid from the cultured microorganism or the medium.

8. A microorganism of the genus *Corynebacterium* producing an L-amino acid, wherein the microorganism comprises the polypeptide of claim 2.

9. A method for producing an L-amino acid, comprising:
(a) culturing the microorganism of claim 8 in a medium to produce an L-amino acid; and
(b) recovering the L-amino acid from the cultured microorganism or the medium.

10. A microorganism of the genus *Corynebacterium* producing an L-amino acid, wherein the microorganism comprises the polypeptide of claim 3.

11. A method for producing an L-amino acid, comprising:
(a) culturing the microorganism of claim 10 in a medium to produce an L-amino acid; and
(b) recovering the L-amino acid from the cultured microorganism or the medium.

* * * * *